United States Patent
Min et al.

(10) Patent No.: US 10,196,452 B2
(45) Date of Patent: Feb. 5, 2019

(54) BINDING MOLECULES TO THE HUMAN OX40 RECEPTOR

(71) Applicants: Pfizer Inc., New York, NY (US); Bristol-Myers Squibb Company, Princeton, NJ (US)

(72) Inventors: Jing Min, Chesterfield, MO (US); Yanli Wu, Ballwin, MO (US); Rory F. Finn, Manchester, MO (US); Barrett R. Thiele, St. Louis, MO (US); Wei Liao, Chesterfield, MO (US); Ronald P. Gladue, Stonington, CT (US); Arvind Rajpal, San Francisco, CA (US); Timothy J. Paradis, Richmond, RI (US); Peter Brams, Sacramento, CA (US); Brigitte Devaux, Palo Alto, CA (US); Yi Wu, Milpitas, CA (US); Kristopher Toy, San Jose, CA (US); Heidi N. Leblanc, Mountain View, CA (US); Haichun Huang, Fremont, CA (US)

(73) Assignees: Pfizer Inc., New York, NY (US); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/807,351

(22) Filed: Nov. 8, 2017

(65) Prior Publication Data
US 2018/0057600 A1   Mar. 1, 2018

Related U.S. Application Data

(62) Division of application No. 14/692,948, filed on Apr. 22, 2015, now Pat. No. 9,840,562, which is a division of application No. 13/474,466, filed on May 17, 2012, now Pat. No. 9,028,824, which is a division of application No. 13/099,196, filed on May 2, 2011, now Pat. No. 8,236,930, which is a division of application No. 12/332,944, filed on Dec. 11, 2008, now Pat. No. 7,960,515.

(60) Provisional application No. 61/013,947, filed on Dec. 14, 2007.

(51) Int. Cl.
*C07K 16/28* (2006.01)
*A61K 39/00* (2006.01)

(52) U.S. Cl.
CPC .... *C07K 16/2878* (2013.01); *A61K 2039/505* (2013.01); *C07K 2317/14* (2013.01); *C07K 2317/21* (2013.01); *C07K 2317/565* (2013.01); *C07K 2317/92* (2013.01)

(58) Field of Classification Search
None
See application file for complete search history.

(56) References Cited

U.S. PATENT DOCUMENTS 7,960,515 B2 * 6/2011 Min ............... C07K 16/2878
530/387.1
8,236,930 B2 * 8/2012 Min ............... C07K 16/2878
530/387.1

* cited by examiner

*Primary Examiner* — Ilia I Ouspenski
(74) *Attorney, Agent, or Firm* — Scully, Scott, Murphy & Presser, P.C.

(57) ABSTRACT

The present disclosure provides isolated binding molecules that bind to the human OX40R, nucleic acid molecules encoding an amino acid sequence of the binding molecules, vectors comprising the nucleic acid molecules, host cells containing the vectors, methods of making the binding molecules, pharmaceutical compositions containing the binding molecules, and methods of using the binding molecules or compositions.

16 Claims, 8 Drawing Sheets

Specification includes a Sequence Listing.

BINDING MOLECULES TO THE HUMAN OX40 RECEPTOR

This application is a division of U.S. application Ser. No. 14/692,948 filed Apr. 22, 2015, which is a division of U.S. application Ser. No. 13/474,466 filed May 17, 2012 (now U.S. Pat. No. 9,028,824 issued May 12, 2015), which is a division of U.S. application Ser. No. 13/099,196 filed May 2, 2011 (now U.S. Pat. No. 8,236,930 issued Aug. 7, 2012), which is a division of U.S. application Ser. No. 12/332,944 filed Dec. 11, 2008 (now U.S. Pat. No. 7,960,515 issued Jun. 14, 2011), which claims the benefit of U.S. Provisional Application No. 61/013,947 filed on Dec. 14, 2007, each of which is incorporated herein by reference in its entirety.

JOINT RESEARCH AGREEMENT

The disclosure and claims herein were made as a result of activities undertaken within the scope of a joint research agreement in effect on or before the date the claimed invention was made between Pfizer Inc. and Medarex, Inc.

BACKGROUND

The present disclosure relates to antibodies, and particularly to antibodies that bind to the OX40 receptor.

Enhancing anti-tumor T cell function represents a powerful and novel approach for cancer treatment. Crucial components involved with generating an effective anti-tumor T cell response include enhancing CD4+ helper T cell activity to promote the generation of anti-tumor cytolytic T cells, and providing survival signals for memory and effector T cells. A key receptor that has been shown to mediate these responses is the OX40 receptor. Sugamura, K., Ishii, N., Weinberg, A. Therapeutic targeting of the effector T-cell co-stimulatory molecule OX40, Nature Rev. Imm. 4: 420-431 (2004); Hori, T. Roles of OX40 in the pathogenesis and control of diseases. Intn. J. Hematology. 83: 17-22 (2006).

The OX40 receptor (OX40R) (also known as CD134, TNFRSF4, ACT-4, ACT35, and TXGP1L) is a member of the TNF receptor superfamily. The OX40R is found to be expressed on activated CD4+ T-cells. High numbers of OX40R+ T cells have been demonstrated within tumors (tumor infiltrating lymphocytes) and in the draining lymph nodes of cancer patients (Vetto, J. T. et al. 1997. Presence of the T-cell activation marker OX-40 on tumor infiltrating lymphocytes and draining lymph nodes cells from patients with melanoma and head and neck cancers. Am. J. Surg. 174: 258-265; Weinberg, A. D. et al. Engagement of the OX-40 receptor in vivo enhances antitumor immunity. J. Immunol. 164: 2160-69 (2000); Petty, J. K., et al. Survival in human colorectal cancer correlates with expression of the T-cell costimulatory molecule OX-40 (CD134). Am. J. Surg. 183: 512-518 (2002)). It was shown in tumor models in mice that engagement of the OX40R in vivo during tumor priming significantly delayed and prevented the appearance of tumors as compared to control treated mice (Weinberg et al., 2000). Therefore, it has been contemplated to enhance the immune response of a mammal to an antigen by engaging the OX40R through the use of an OX40R binding agent (WO 99/42585; Weinberg et al., 2000).

SUMMARY

The present disclosure provides isolated binding molecules that bind to the human OX40R, including OX40R antibodies, antigen-binding fragments of the OX40R antibodies, and derivatives of the OX40R antibodies. In some embodiments the binding molecule binds to the human OX40R with a $K_D$ of $1 \times 10^{-7}$ M or less and has agonist activity on the human OX40R. In some further embodiments, the binding molecule is a human monoclonal antibody that specifically binds to the human OX40R with a $K_D$ of 100 nM or less.

The present disclosure also provides a composition that comprises one or more of the binding molecules and a pharmaceutically acceptable carrier. In some embodiments, the binding molecule is a human monoclonal OX40R antibody or an antigen-binding fragment thereof. The composition may further comprise additional pharmaceutical agents, such as chemotherapeutic agents, immunotherapeutic agents, and hormonal therapeutic agents.

The present disclosure further provides therapeutic and diagnostic methods using the binding molecules. In some embodiments, the disclosure provides a method of treating or preventing cancer in a mammal, comprising administering to the mammal a therapeutically effective amount of a binding molecule or a composition comprising a binding molecule. In some other embodiments, the disclosure provides a method of enhancing an immune response in a mammal, comprising administering to the mammal a therapeutically effective amount of a binding molecule or a composition comprising a binding molecule. In some particular embodiments the binding molecule used in the methods is a human monoclonal OX40R antibody or an antigen-binding fragment thereof.

The present disclosure further provides nucleic acid molecules that encode an amino acid sequence of a binding molecule, vectors comprising such nucleic acids, host cells comprising the vectors, and methods of preparing the binding molecules.

The disclosure also provides other aspects, which will be apparent from the entire disclosure, including the claims.

DETAILED DESCRIPTION

Definitions

Figure 1A:
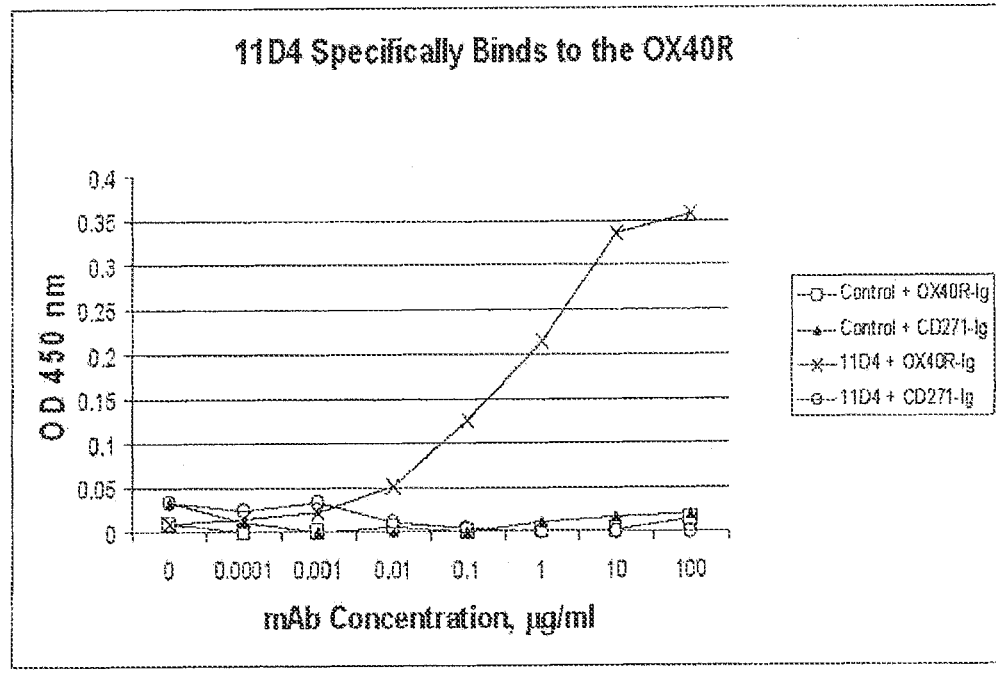
FIGS. 1a and 1b are graphs showing that antibody 11D4 specifically binds to the OX40R.

The term "agonist" refers to a binding molecule, as defined herein, which upon binding to the OX40R, (1) stimulates or activates the OX40R, (2) enhances, increases, promotes, induces, or prolongs an activity, function, or presence of the OX40R, or (3) enhances, increases, promotes, or induces the expression of the OX40R.

The term "antibody" refers to an immunoglobulin molecule that is typically composed of two identical pairs of polypeptide chains, each pair having one "light" (L) chain and one "heavy" (H) chain. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 3 or more amino acids. Each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, CL. The constant regions of the antibodies may mediate the binding of the immunoglobulin to host tissues or factors, including various cells of the immune system (e.g., effector cells) and the first component (C1q) of the classical complement system. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of each heavy/light chain pair ($V_H$ and $V_L$), respectively, form the antibody binding site. The assignment of amino acids to each region or domain is in accordance with the definitions of Kabat Sequences of Proteins of Immunological Interest (National Institutes of Health, Bethesda, Md. (1987 and 1991)), or Chothia & Lesk (1987) J. Mol. Biol. 196:901-917; Chothia et al. (1989) Nature 342:878-883. The term "antibody" encompasses an antibody that is part of an antibody multimer (a multimeric form of antibodies), such as dimers, trimers, or higher-order multimers of monomeric antibodies. It also encompasses an antibody that is linked or attached to, or otherwise physically or functionally associated with, a non-antibody moiety. Further, the term "antibody" is not limited by any particular method of producing the antibody. For example, it includes, inter alia, recombinant antibodies, monoclonal antibodies, and polyclonal antibodies.

The term "antibody derivative" or "derivative" of an antibody refers to a molecule that is capable of binding to the same antigen (e.g., OX40R) that the antibody binds to and comprises an amino acid sequence of the antibody linked to an additional molecular entity. The amino acid sequence of the antibody that is contained in the antibody derivative may be the full-length antibody, or may be any portion or portions of a full-length antibody. The additional molecular entity may be a chemical or biological molecule. Examples of additional molecular entities include chemical groups, amino acids, peptides, proteins (such as enzymes, antibodies), and chemical compounds. The additional molecular entity may have any utility, such as for use as a detection agent, label, marker, pharmaceutical or therapeutic agent. The amino acid sequence of an antibody may be attached or linked to the additional entity by chemical coupling, genetic fusion, noncovalent association or otherwise. The term "antibody derivative" also encompasses chimeric antibodies, humanized antibodies, and molecules that are derived from modifications of the amino acid sequences of an OX40R antibody, such as conservation amino acid substitutions, additions, and insertions.

The term "antigen-binding fragment" of an antibody refers to one or more portions of a full-length antibody that retain the ability to bind to the same antigen (e.g., OX40R) that the antibody binds to. The term "antigen-binding fragment" also encompasses the portion of an antibody that is part of a larger molecule formed by covalent or noncovalent association of the antibody portion with one or more additional molecular entities. Examples of additional molecular entities include amino acids, peptides, or proteins, such as the streptavidin core region, which may be used to make a tetrameric scFv molecule (Kipriyanov et al., (1995) Human Antibodies and Hybridomas 6:93-101), a cysteine residue, a marker peptide, or a C-terminal polyhistidine tag, which may be used to make bivalent and biotinylated scFv molecules (Kipriyanov et al., (1994) Mol. Immunol. 31:1047-1058).

The term "binding molecule" encompasses (1) antibody, (2) antigen-binding fragment of an antibody, and (3) derivative of an antibody, each as defined herein.

The term "binds to OX40R" or "binding to OX40R" refers to the binding of a binding molecule, as defined herein, to the OX40R in an in vitro assay, such as a BIAcore assay. Binding means a binding affinity ($K_D$) of $1 \times 10^{-6}$ M or less.

The term "chimeric antibody" refers to an antibody that comprises amino acid sequences derived from two or more different antibodies. The two or more different antibodies may be from the same species or from two or more different species.

The term "conservative amino acid substitution" refers to substitution of an amino acid residue by another amino add residue, wherein the side chain R groups of the two amino acid residues have similar chemical properties (e.g., charge or hydrophobicity). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acid substitution groups can be, for example, valine-leucine-isoleucine, phenylalanine-tyrosine, lysine-arginine, alanine-valine, glutamate-aspartate, and asparagine-glutamine.

The term "epitope" refers to the part of an antigen that is capable of specific binding to an antibody, or T-cell receptor, or otherwise interacting with a molecule. "Epitope" is also known in the art as "antigenic determinant." An epitope generally consists of chemically active surface groupings of molecules such as amino acids or carbohydrate or sugar side chains and generally have specific three dimensional structural characteristics, as well as specific charge characteristics. An epitope may be "linear" or "conformational." Once a desired epitope on an antigen is determined, antibodies to that epitope can be generated, e.g., using the techniques described herein. The generation and characterization of antibodies may also elucidate information about desirable epitopes. From this information, it is then possible to competitively screen antibodies for binding to the same epitope. An approach to achieve this is to conduct cross-competition studies to find antibodies that competitively bind with one another, i.e., the antibodies compete for binding to the antigen. A high throughput process for "binning" antibodies based upon their cross-competition is described in PCT Publication No. WO 03/48731.

The term "germline" refers to the nucleotide sequences of the antibody genes and gene segments as they are passed from parents to offspring via the germ cells. The germline sequence is distinguished from the nucleotide sequences encoding antibodies in mature B cells which have been altered by recombination and hypermutation events during the course of B cell maturation.

The term "host cell" refers to a cell into which an expression vector has been introduced. The term encompasses not only the particular subject cell but also the progeny of such a cell. Because certain modifications may occur in succeeding generations due to either mutation or environmental influences, such progeny may not be identical to the parent cell, but are still included within the scope of the term "host cell." The term "human antibody" refers to an antibody consisting of amino acid sequences of human immunoglobulin sequences only. A human antibody may contain murine carbohydrate chains if produced in a mouse, in a mouse cell or in a hybridoma derived from a mouse cell. Human antibodies may be prepared in a variety of ways known in the art.

The term "humanized antibody" refers to a chimeric antibody that contains amino acid residues derived from human antibody sequences. A humanized antibody may contain some or all of the CDRs from a non-human animal antibody while the framework and constant regions of the antibody contain amino acid residues derived from human antibody sequences.

The term "mammal" refers to any animal species of the Mammalia class. Examples of mammals include: humans; laboratory animals such as rats, mice, simians and guinea pigs; domestic animals such as cats, dogs, rabbits, cattle, sheep, goats, horses, and pigs; and captive wild animals such as lions, tigers, elephants, and the like.

The term "isolated nucleic acid" refers to a nucleic acid molecule of genomic, cDNA, or synthetic origin, or a combination thereof, which is separated from other nucleic acid molecules present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid of interest) in the genomic DNA of the organism from which the nucleic acid is derived.

The term "isolated antibody" or "isolated binding molecule" refers to an antibody or a binding molecule that: (1) is not associated with naturally associated components that accompany it in its native state; (2) is free of other proteins from the same species; (3) is expressed by a cell from a different species; or (4) does not occur in nature. Examples of isolated antibodies include an OX40R antibody that has been affinity purified using OX40R, an OX40R antibody that has been generated by hybridomas or other cell line in vitro, and a human OX40R antibody derived from a transgenic animal.

The term "$K_D$" refers to the equilibrium dissociation constant of a particular antibody-antigen interaction and is used to describe the binding affinity between a ligand (such as an antibody) and a protein (such as the OX40R). The smaller the equilibrium dissociation constant, the more tightly bound the ligand is, or the higher the affinity between ligand and protein. A $K_D$ can be measured by surface plasmon resonance, for example using the BIACORE™ system. An assay procedure using the BIACORE™ system (BIAcore assay) is described in the Examples section of this disclosure.

The term "off rate" or "kd" refers to the dissociation rate constant of a particular antibody-antigen interaction. A dissociation rate constant can be measured by surface plasmon resonance, for example using the BIACORE™.

The term "OX40R antibody" refers to an antibody, as defined herein, capable of binding to the human OX40R.

The terms "OX40 receptor" and "OX40R" are used interchangeably in the present application, and include the human OX40R, as well as variants, isoforms, and species homologs thereof. Accordingly, human binding molecules disclosed herein may, in certain cases, also bind to the OX40R from species other than human. In other cases, the binding molecules may be completely specific for the human OX40R and may not exhibit species or other types of cross-reactivity.

The term "specifically bind to the human OX40R" in reference to the interaction of a binding molecule, e.g., an antibody, with its binding partner, e.g., an antigen, means that the $K_D$ of a binding molecule for binding to CD40, CD137, or CD271 is more than 100 fold the $K_D$ for its binding to the human OX40R, as determined in an in vitro assay.

The term "vector" refers to a nucleic acid molecule capable of transporting another nucleic acid molecule in a host cell. Examples of vectors include plasmids, viral vectors, naked DNA or RNA expression vectors, cosmid or phage vectors. Some vectors are capable of autonomous replication in a host cell into which they are introduced (e.g., bacterial vectors having a bacterial origin of replication and episomal mammalian vectors). Some vectors can be integrated into the genome of a host cell upon introduction into the host cell, and thereby are replicated along with the host genome (e.g., non-episomal mammalian vectors). Certain vectors are capable of directing the expression of genes to which they are operatively linked, and therefore may be referred to as "expression vectors."

As used herein, the twenty conventional amino acids and their abbreviations follow conventional usage. See Immunology—A Synthesis ($2^{nd}$ Edition, E. S. Golub and D. R. Gren, Eds., Sinauer Associates, Sunderland, Mass. (1991)).

Binding Molecules that Bind to the Human OX40R

The present disclosure provides isolated binding molecules that bind to the human OX40R, including OX40R antibodies, antigen-binding fragments of the OX40R antibodies, and derivatives of the OX40R antibodies. The binding molecules are characterized by at least one of the following functional properties: (a) bind to the human OX40R with a $K_D$ of $1\times10^{-6}$ M or less; (b) have agonist activity on the human OX40R; (c) do not bind to CD40 receptor at concentration up to 500 nM; (d) do not bind to CD137 receptor at concentrations up to 500 nM; (e) do not bind to CD271 receptor at concentrations up to 500 nM; (f) are capable of enhancing IL-2 production by isolated human T cells; (g) are capable of enhancing immune response; (h) are capable of inhibiting tumor cell growth; and (i) have therapeutic effect on a cancer. In some embodiments the binding molecule binds to the human OX40R with a $K_D$ of $1\times10^{-7}$ M or less, or $1\times10^{-8}$ M or less, or $5\times1\times10^{-9}$ M or less.

Human OX40R Antibodies

In some first aspects, the present disclosure provides a human antibody that binds to the human OX40R. In some embodiments, the human antibody is a monoclonal antibody that specifically binds to the human OX40R with a $K_D$ of 100 nM or less, preferably 10 nM or less, and has agonist activity on the human OX40R. One example of such human antibodies is the human monoclonal antibody 11D4. The amino acid sequence of the heavy chain and amino acid sequence of the variable region of the heavy chain ($V_H$) of antibody 11D4 are shown in SEQ ID NOs: 9 and 7, respectively. The amino acid sequence of the light chain and the amino acid sequence of the variable region of the light chain ($V_L$) of antibody 11D4 are shown in SEQ ID NOS: 10 and 8, respectively. The isotypes of antibody 11D4 are IgG2 for the heavy chain and Kappa for the light chain. The allotypes of antibody 11D4 are G2(n−) for the heavy chain and Km3 for the light chain. The mature heavy and light chain amino acid sequences are derived from conceptual translation of DNA sequences in the expression constructs. Antibody 11D4 contains no framework mutations in the heavy chain or light chain, but contains one mutation in the heavy chain CDR2.

Another illustrative antibody of the disclosure is the human monoclonal antibody 18D8. The amino acid sequence of the $V_H$ region and $V_L$ region of antibody 18D8 is shown in SEQ ID NOs: 19 and 20, respectively. The amino acid sequence of the heavy chain and light chain is shown in SEQ ID NOS: 21 and 22, respectively.

Given that 11D4 and 18D8 bind to the OX40R, the $V_H$ and $V_L$ sequences of each of them can be "mixed and matched" with other OX40R antibodies to create additional antibodies. The binding of such "mixed and matched" antibodies to the OX40R can be tested using the binding assays known in the art, including an assay described in the Examples. In one case, when $V_H$ and $V_L$ regions are mixed and matched, a $V_H$ sequence from a particular $V_H/V_L$ pairing is replaced with a structurally similar $V_H$ sequence. Likewise, in another case a $V_L$ sequence from a particular $V_H/V_L$ pairing is replaced with a structurally similar $V_L$ sequence.

Accordingly, in some embodiments, the disclosure provides an isolated OX40R antibody that comprises: (1) a heavy chain variable region of antibody 11D4 or 18D8, (2) a heavy chain variable region comprising an amino acid sequence of SEQ ID NOs: 7 or 19, or (3) a heavy chain variable region comprising an amino acid sequence encoded by a nucleic acid sequence of SEQ ID NOs: 11 or 23. In some other embodiments, the disclosure provides an isolated OX40R antibody that comprises: (1) a light chain variable region of antibody 11D4 or 18D8, (2) a light chain variable region comprising an amino acid sequence of SEQ ID NOs: 8 or 20, or (3) light chain variable region comprising an amino acid sequence encoded by a nucleic acid sequence of SEQ ID NOs: 12 or 24.

In another aspect, the disclosure provides antibodies that comprise the CDR1, CDR2, and CDR3 of the heavy chain variable region ($V_H$) and CDR1, CDR2, and CDR3 of the light chain of 11D4 or 11D8. The amino acid sequence of the $V_H$ CDR1, $V_H$ CDR2, and $V_H$ CDR3 of 11D4 is shown in SEQ ID NOs: 1, 2, and 3, respectively. The amino acid sequence of the $V_L$ CDR1, $V_L$ CDR2, and $V_L$ CDR3 of antibody 11D4 is shown in SEQ ID NOs: 4, 5, and 6, respectively. The amino acid sequence of the $V_H$ CDR1, $V_H$ CDR2, and $V_H$ CDR3 of antibody 18D8 is shown in SEQ ID NOs: 13, 14, and 15, respectively. The amino acid sequence of the $V_L$ CDR1, $V_L$ CDR2, and $V_L$ CDR3 of antibody 18D8 is shown in SEQ ID NOs: 16, 17, and 18, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that 11D4 and 18D8 bind to the human OX40R and that antigen-binding specificity is provided primarily by the CDR1, CDR2, and CDR3 regions, the $V_H$ CDR1, CDR2, and CDR3 sequences and $V_L$ CDR1, CDR2, and CDR3 sequences can be "mixed and matched" to create additional OX40R antibodies. For example, CDRs from different OX40R antibodies can be mixed and matched, although each antibody will typically contain a $V_H$ CDR1, CDR2, and CDR3 and a $V_L$ CDR1, CDR2, and CDR3. The binding of such "mixed and matched" antibodies to the OX40R can be tested using the binding assays described above and in the Examples (e.g., ELISAs, Biacore analysis). In one case, when $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence typically is replaced with a structurally similar CDR sequence(s). It will be readily apparent to an ordinarily skilled artisan that novel $V_H$ and $V_L$ sequences can be created by substituting one or more $V_H$ and/or $V_L$ CDR region sequences with structurally similar sequences from the CDR sequences disclosed herein.

Accordingly, in some embodiments, the disclosure provides (1) an isolated monoclonal antibody that comprises at least one CDR selected from $V_H$ CDR1, $V_H$ CDR2, or $V_H$ CDR3 of antibody 11D4 or 18D8. In some other embodiments, the disclosure provides an isolated monoclonal antibody that comprises at least one CDR selected from $V_L$ CDR1, $V_L$ CDR2 or $V_L$ CDR3 of antibody 11D4 or 18D8. In some further embodiments, the disclosure provides an isolated monoclonal antibody that comprises at least one CDR selected from: a $V_H$ CDR1 comprising the amino acid sequence of SEQ ID NOs: 1 or 13, or a sequence that differs from SEQ ID NOs: 1 or 3 by 1, 2, 3, or 4 conservative amino acid substitutions; a $V_H$ CDR2 comprising the amino acid sequence of SEQ ID NOs: 2 or 14 or a sequence that differs from SEQ ID NOs: 2 or 14 by 1, 2, 3, or 4 conservative amino acid substitutions; and a $V_H$ CDR3 comprising the amino acid sequence of SEQ ID NOs: 3 or 15 or a sequence that differs from SEQ ID NOs: 3 or 15 by 1, 2, 3, or 4 conservative amino acid substitutions.

In still some further embodiments, the disclosure provides an isolated monoclonal antibody that comprises at least one CDR selected from: a $V_L$ CDR1 comprising the amino acid sequence of SEQ ID NOs: 4 or 16 or a sequence that differs from SEQ ID NOs: 4 or 16 by 1, 2, 3, or 4 conservative amino acid substitutions; a $V_L$ CDR2 comprising the amino acid sequence of SEQ ID NOs: 5 or 17 or a sequence that differs from SEQ ID NOs: 5 or 17 by 1, 2, 3, or 4 conservative amino acid substitutions; and a $V_L$ CDR3 comprising the amino acid sequence of SEQ ID NOs: 6 or 18 or a sequence that differs from SEQ ID NOs: 6 or 18 by 1, 2, 3, or 4 conservative amino acid substitutions.

In some cases, the C-terminal lysine of the heavy chain of an OX40R antibody is cleaved (Harris R. J., *J. of Chromotography*, 705: 129-134 (1995)). The heavy and/or light chain(s) of the OX40R antibodies may optionally include a signal sequence.

The class (e.g., IgG, IgM, IgE, IgA, or IgD) and subclass (e.g., IgG1, IgG2, IgG3, or IgG4) of the OX40R antibodies may be determined by any suitable method. In general, the class and subclass of an antibody may be determined using antibodies that are specific for a particular class and subclass of antibody. Such antibodies are commercially available. The class and subclass can be determined by ELISA, or Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies. The OX40R antibodies can be an IgG, an IgM, an IgE, an IgA, or an IgD molecule. For example, the OX40R antibodies can be an IgG that is an IgG1, IgG2, IgG3, or an IgG4 subclass. Thus, another aspect of the disclosure provides a method for converting the class or subclass of an OX40R antibody to another class or subclass. In some cases, a nucleic acid molecule encoding a $V_L$ or $V_H$ that does not include sequences encoding $C_L$ or $C_H$ is isolated using methods well-known in the art. The nucleic acid molecule then is operatively linked to a nucleic acid sequence encoding a $C_L$ or $C_H$ from a desired immunoglobulin class or subclass. This can be achieved using a vector or nucleic acid molecule that comprises a $C_L$ or $C_H$ chain, as described above. For example, an OX40R antibody that was originally IgM can be class switched to an IgG. Further, the class switching may be used to convert one IgG subclass to another, e.g., from IgG1 to IgG2. Another method for producing an antibody comprising a desired isotype comprises the steps of isolating a nucleic acid encoding a heavy chain of an OX40R antibody and a nucleic acid encoding a light chain of an OX40R antibody, isolating the sequence encoding the $V_H$ region, ligating the $V_H$ sequence to a sequence encoding a heavy chain constant domain of the desired isotype, expressing the light chain gene and the heavy chain construct in a cell, and collecting the OX40R antibody with the desired isotype.

Antigen-Binding Fragments

In another aspect, the present disclosure provides antigen-binding fragments of any of the human OX40R antibodies as described herein above. In some embodiments, the antigen-binding fragment is selected from: (1) a light chain of an OX40R antibody; (2) a heavy chain of an OX40R antibody; (3) a variable region from the light chain of an OX40R antibody; (4) a variable region from the heavy chain of an OX40R antibody; (5) one or more CDRs (two, three, four, five, or six CDRs) of an OX40R antibody; or (6) three CDRs from the light chain and three CDRs from the heavy chain of an OX40R antibody. In some particular embodiments, the disclosure provides an antigen-binding fragment of antibody 11D4 or 18D8. In some other particular embodiments, the antigen-binding fragments of an OX40R antibody include: (i) a Fab fragment, a monovalent fragment consisting of the $V_L$, $V_H$, $C_L$ and $C_H 1$ domains; (ii) a F(ab')$_2$ fragment, a bivalent fragment comprising two Fab fragments linked by a disulfide bridge at the hinge region; (iii) a Fd fragment consisting of the $V_H$ and $C_H 1$ domains; (iv) a Fv fragment consisting of the $V_L$ and $V_H$ domains of a single arm of an antibody; (v) a dAb fragment (Ward et al., (1989) Nature 341:544-546), which consists of a $V_H$ domain; (vi) an isolated CDR, and (vii) single chain antibody (scFv), which is a polypeptide comprising a $V_L$ region of an antibody linked to a $V_H$ region of an antibody. Bird et al., (1988) Science 242:423-426 and Huston et al., (1988) Proc. Natl. Acad. Sci. USA 85:5879-5883. An antigen-binding fragment may also comprise two or more shorter fragments, either from the same heavy drain or same light chain, or from different chains. Antigen-binding fragments, such as Fab and F(ab')$_2$ fragments, can be prepared from whole antibodies using conventional techniques, such as papain or pepsin digestion, respectively, of whole antibodies. They can also be obtained using recombinant DNA techniques, as described herein.

Antibody Derivatives

In some further aspects, the present disclosure provides derivatives of any of the OX40R antibodies as described herein above.

In one particular aspect, the antibody derivative is derived from modifications of the amino acid sequences of 11D4 or 18D8. Amino acid sequences of any regions of the antibody chains may be modified, such as framework regions, CDR regions, or constant regions. The modifications can be introduced by standard techniques known in the art, such as site-directed mutagenesis and random PCR-mediated mutagenesis, and may comprise natural as well as non-natural amino acids.

Types of modifications include substitutions, insertions, deletions, or combinations thereof, of one or more amino acids of an OX40R antibody. In some embodiments, the antibody derivative comprises 1, 2, 3, or 4 amino acid substitutions in the heavy chain CDRs and/or one amino acid substitution in the light chain CDRs. In some embodiments, a derivative of an OX40R antibody comprises one or more amino acid substitutions relative to the germline amino acid sequence of the human gene. In a particular embodiment, one or more of those substitutions from germline is in the CDR2 region of the heavy chain. In another particular embodiment, the amino acid substitutions relative to the germline are at one or more of the same positions as the substitutions relative to germline in antibodies 11D4 or 18D8. In another embodiment, the amino acid substitution is to change one or more cysteines in an antibody to another residue, such as, without limitation, alanine or serine. The cysteine may be a canonical or non-canonical cysteine. The substitution can be made in a CDR or framework region of a variable domain or in the constant domain of an antibody. Another type of amino acid substitution is to eliminate asparagine-glycine pairs, which form potential deamidation sites, by altering one or both of the residues. In still other embodiments, the amino acid substitution is a conservative amino acid substitution. In one embodiment, the antibody derivative has 1, 2, 3, or 4 conservative amino acid substitutions in the heavy chain CDR regions relative to the amino acid sequences of 11D4 or 18D8.

Another type of modification of an OX40R antibody is the alteration of the original glycosylation pattern of the antibody. The term "alteration" refers to deletion of one or more carbohydrate moieties found in the antibody, and/or adding one or more glycosylation sites that are not present in the antibody. Glycosylation of antibodies is typically N-linked.

N-linked refers to the attachment of the carbohydrate moiety to the side chain of an asparagine residue. Addition of glycosylation sites to the antibody is conveniently accomplished by altering the amino acid sequence such that it contains one or more of the above-described tripeptide sequences (for N-linked glycosylation sites).

Still another type of modification involves removal of any carbohydrate moieties present on the antibody which may be accomplished chemically or enzymatically. Chemical deglycosylation requires exposure of the antibody to a compound, such as trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr, H. T., and Bahl, O. P., Arch. Biochem. Biophys. 259 (1987) 52-57 and by Edge, A. S., et al. Anal. Biochem. 118 (1981) 131-137. Enzymatic cleavage of carbohydrate moieties on antibodies can be achieved by the use of a variety of endo- and exo-glycosidases as described by Thotakura, N. R., and Bahl, O. P., Meth. Enzymol. 138 (1987) 350-359.

Examples of other modifications include acetylation, acylation, amidation, cross-linking, cyclization, disulfide bond formation, demethylation, formation of covalent cross-links, formation of cystine, formylation, hydroxylation, iodination, methylation, myristoylation, oxidation, pegylation, proteolytic processing, phosphorylation, prenylation, and sulfation.

In a further aspect, there is provided an antibody derivative that comprises an OX40R antibody, or antigen-binding fragment thereof, as described herein, linked to an additional molecular entity. Examples of additional molecular entities include pharmaceutical agents, peptides or proteins, and detection agent or labels. Specific examples of pharmaceutical agents that may be linked to an OX40R antibody include cytotoxic agents or other cancer therapeutic agents, and radioactive isotopes. Specific examples of peptides or proteins that may be linked to an OX40R antibody include antibodies, which may be the same OX40R antibody or a different antibody. Specific examples of detection agents or labels that may be linked to an OX40R antibody include (1) fluorescent compounds, such as fluorescein, fluorescein isothiocyanate, rhodamine, 5-dimethylamine-1-naphthalenesulfonyl chloride, phycoerythrin, and lanthanide phosphors; (2) enzymes, such as horseradish peroxidase, β-galactosidase, luciferase, alkaline phosphatase, and glucose oxidase; (3) biotin; (4) a predetermined polypeptide epitope recognized by a secondary reporter, such as leucine zipper pair sequences, binding sites for secondary antibodies, metal binding domains, and epitope tags. In a particular embodiment, the antibody derivative is an OX40R antibody multimer, which is a multimeric form of an OX40R antibody, such as antibody dimers, trimers, or higher-order multimers of monomeric antibodies. Individual monomers within an antibody multimer may be identical or different, i.e., they may be heteromeric or homomeric antibody multimers. Individual antibodies within a multimer may have the same or different binding specificities. Multimerization of antibodies may be accomplished through natural aggregation of antibodies. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art, such as through using heterobifunctional crosslinking agents. Suitable crosslinkers include those that are heterobifunctional, having two distinctly reactive groups separated by an appropriate spacer (such as m-maleimidobenzoyl-N-hydroxysuccinimide ester, succinimidyl 4-(maleimidomethyl)cyclohexane-1-carboxylate, and N-succinimidyl S-acethylthioacetate) or homobifunctional (such as disuccinimidyl suberate). Such linkers are commercially available from Pierce Chemical Company, Rockford, Ill. Antibodies can also be made to multimerize through recombinant DNA techniques known in the art.

In still another aspect, the antibody derivative is a chimeric antibody, which comprises an amino acid sequence of a human OX40R antibody described herein above. In one example, one or more CDRs from a human OX40R antibody is combined with CDRs from an antibody from a non-human animal, such as mouse or rat. In another example, all of the CDRs of the chimeric antibody are derived from human OX40R antibodies. In another example, the CDRs from more than one human OX40R antibody are combined in a chimeric antibody. Further, a chimeric antibody may comprise the framework regions derived from one human OX40R antibody and one or more CDRs from one or more different human antibodies. Chimeric antibodies can be generated using conventional methods known in the art. In some particular embodiments, the chimeric antibody comprises one, two, or three CDRs from the heavy chain variable region or from the light chain variable region of an antibody selected from antibody 11D4 or 18D8.

Examples of other antibody derivatives provided by the present disclosure include single chain antibodies, diabodies, domain antibodies, nanobodies, and unibodies. A "single-chain antibody" (scFv) consists of a single polypeptide chain comprising a $V_L$ domain linked to a $V_H$ domain wherein $V_L$ domain and $V_H$ domain are paired to form a monovalent molecule. Single chain antibody can be prepared according to method known in the art (see, for example, Bird et al., (1988) Science 242:423-426 and Huston et al., (1988) Proc. Natl. Acad. Sci. USA 85:5879-5883). A "diabody" consists of two chains, each chain comprising a heavy chain variable region connected to a light chain variable region on the same polypeptide chain connected by a short peptide linker, wherein the two regions on the same chain do not pair with each other but with complementary domains on the other chain to form a bispecific molecule. Methods of preparing diabodies are known in the art (See, e.g., Holliger P. et al., (1993) Proc. Natl. Acad. Sci. USA 90:6444-6448, and Poljak R. J. et al., (1994) Structure 2:1121-1123). Domain antibodies (dAbs) are small functional binding units of antibodies, corresponding to the variable regions of either the heavy or light chains of antibodies. Domain antibodies are well expressed in bacterial, yeast, and mammalian cell systems. Further details of domain antibodies and methods of production thereof are known in the art (see, for example, U.S. Pat. Nos. 6,291,158; 6,582,915; 6,593,081; 6,172,197; 6,696,245; European Patents 0368684 & 0616640; WO05/035572, WO04/101790, WO04/081026, WO04/058821, WO04/003019 and WO03/002609. Nanobodies are derived from the heavy chains of an antibody. A nanobody typically comprises a single variable domain and two constant domains (CH2 and CH3) and retains antigen-binding capacity of the original antibody. Nanobodies can be prepared by methods known in the art (See e.g., U.S. Pat. No. 6,765,087, U.S. Pat. No. 6,838,254, WO 06/079372). Unibodies consist of one light chain and one heavy chain of a IgG4 antibody. Unibodies may be made by the removal of the hinge region of IgG4 antibodies. Further details of unibodies and methods of preparing them may be found in WO2007/059782.

Methods of Producing the Binding Molecules

Binding molecules as disclosed herein can be produced by techniques known in the art, including conventional monoclonal antibody methodology, e.g., the standard somatic cell hybridization technique of Köhler and Milstein (Nature 256: 495, (1975)), as well as other techniques such as viral or oncogenic transformation of B lymphocytes.

Immunization of Non-Human Animals

The disclosure also provides a method for making OX40R antibodies or antigen-binding fragments thereof, which comprises immunizing a non-human animal that comprises human immunoglobulin loci with an OX40R antigen, and isolating the antibody from the immunized animal or from cells derived from the immunized animal.

Examples of suitable non-human animals include a transgenic or transchromosomic animal, such as HuMAb Mouse®, KM Mouse®, "TC mice," and Xenomouse™. The HuMAb Mouse® (Medarex, Inc.) contains human immunoglobulin gene miniloci that encode unrearranged human heavy (µ and γ) and κ light chain immunoglobulin sequences, together with targeted mutations that inactivate the endogenous µ and κ chain loci (see e.g., Lonberg, et al. (1994) Nature 368: 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (See, e.g., Harding, F. and Lonberg, N. (1995) Ann. N.Y. Acad. Sci. 764:536-546). Preparation and use of the HuMAb Mouse®, and the genomic modifications carried by such mice, is well know in the art (See, e.g., Fishwild, D. et al. (1996) Nature Biotechnology 14: 845-851). The KM Mice™ carry a human heavy chain transgene and a human light chain transchromosome and are described in detail in WO 02/43478. The Xenomouse™ (Abgenix, Inc.) contains large fragments of the human immunoglobulin loci and is deficient in mouse antibody production. This animal model is well known in the art (See, e.g., U.S. Pat. Nos. 5,939,598; 6,075,181; 6,114,598; 6,150,584; and 6,162,963). "TC mice" are also engineered mice carrying both a human heavy chain transchromosome and a human light chain transchromosome. Such mice are described in Tomizuka et al. (2000) Proc. Natl. Acad. Sci. USA 97:722-727.

The OX40R antigen for use to immunize the animal may be isolated and/or purified OX40 and is preferably a human OX40R. In one embodiment, the OX40R antigen is a fragment of the human OX40R, preferably the extracellular domain of the OX40R. In another embodiment, the OX40R antigen is a fragment that comprises at least one epitope of the human OX40R. In another embodiment, the OX40R antigen is a cell that expresses OX40R on its cell surface, more particularly a cell that overexpresses the OX40R on its cell surface. Immunization of the animals may be done by any suitable method known in the art. (See, e.g., Harlow and Lane, Antibodies: A Laboratory Manual, New York: Cold Spring Harbor Press, 1990). Particular methods for immunizing non-human animals such as mice, rats, sheep, goats, pigs, cattle and horses are well known in the art (See, e.g., Harlow and Lane (1990); U.S. Pat. No. 5,994, 619). Example 1 provides a method for immunizing HuMab mice.

After immunization of the animal with an OX40R antigen, antibodies and/or antibody-producing cells can be obtained from the animal. In one embodiment, serum is obtained from the animal and an immunoglobulin fraction may be obtained from the serum, or the OX40R antibodies may be purified from the serum.

The OX40R antibodies may also be produced using antibody-producing immortalized cells prepared from cells isolated from the immunized animal. After immunization, the lymph node and/or splenic B cells are collected from the animal and immortalized by suitable means. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene (See, e.g., Harlow and Lane, supra). In a particular embodiment, the splenic B cells, collected from the immunized animal are fused to immortalized myeloma cells to form antibody-producing immortalized hybridomas. The myeloma cells preferably do not secrete immunoglobulin polypeptides (a non-secretory cell line). Immortalized hybridomas are screened using the OX40 antigen (e.g., the OX40R, a portion thereof, or a cell expressing the OX40R). The initial screening may be performed, for example, using an enzyme-linked immunoassay (ELISA) or a radioimmunoassay. An example of ELISA screening is described in WO 00/37504.

The OX40R antibody-producing cells, e.g., hybridomas, are selected, cloned, and further screened for desirable characteristics, including robust growth, high antibody production, and desirable antibody characteristics, as discussed further below. Hybridomas can be expanded in vivo in syngeneic animals, in animals that lack an immune system, e.g., nude mice, or in cell culture in vitro.

Thus, methods are provided for producing a cell that produces a human monoclonal OX40R antibody or an antigen-binding fragment thereof, comprising: (a) immunizing a non-human transgenic animal with an OX40R antigen; (b) allowing the animal to mount an immune response to the OX40R antigen; (c) isolating antibody-producing cells from the animal; and (d) immortalizing the antibody-producing cells. In one embodiment, the method further comprises (e) creating individual monoclonal populations of the immortalized antibody-producing cells; and (f) screening the immortalized antibody-producing cells that produce a desired OX40R antibody.

Nucleic Acids, Vectors, Host Cells, and Recombinant Methods of Producing OX40R Antibodies Another aspect of the disclosure provides an isolated nucleic acid molecule encoding an amino acid sequence of a binding molecule that binds the human OX40R. The amino acid sequence encoded by the nucleic acid molecule may be any portion of an intact antibody, such as a CDR, a sequence comprising one, two, or three CDRs, or a variable region of a heavy chain or light chain, or may be a full-length heavy chain or light chain. In some embodiments, the nucleic acid molecule encodes an amino acid sequence that comprises (1) a CDR3 region, particularly a heavy chain CDR3 region, of antibodies 11D4 or 18D8; (2) a variable region of a heavy chain or variable region of a light chain of antibodies 11D4 or 18D8; or (3) a heavy chain or a light chain of antibodies 11D4 or 18D8. In other embodiments, the nucleic acid molecule encodes a polypeptide that comprises an amino acid sequence selected from the group consisting of SEQ ID NOs: 1, 2, 3, 4, 5, 6, 7, 8, 9, 10, 13, 14, 15, 16, 17, 18, 19, 20, 21, and 22. In still other embodiments, the nucleic acid molecule is selected from the group consisting of SEQ ID NOs: 11, 12, 23, and 24.

The nucleic acid molecules provided by the disclosure may be obtained from any source that produces an OX40R antibody. mRNA from OX40R antibody-producing cells may be isolated by standard techniques, cloned and/or amplified using PCR and library construction techniques, and screened using standard protocols to obtain nucleic acid molecules encoding an amino acid sequence of an OX40R antibody. The mRNA may be used to produce cDNA for use in the polymerase chain reaction (PCR) or cDNA cloning of antibody genes. In one embodiment, the nucleic acid molecule is obtained from a hybridoma that expresses an OX40R antibody, as described above, preferably a hybridoma that has as one of its fusion partners a non-human transgenic animal cell that expresses human immunoglobulin genes. In another embodiment, the hybridoma is derived from a non-human, non-transgenic animal.

A nucleic acid molecule encoding the heavy chain of an OX40R antibody may be constructed by fusing a nucleic acid molecule encoding the heavy variable region with a nucleic acid molecule encoding a constant region of a heavy chain. Similarly, a nucleic acid molecule encoding the light chain of an OX40R antibody may be constructed by fusing a nucleic acid molecule encoding the light chain variable region with a nucleic acid molecule encoding a constant region of a light chain. The nucleic acid molecules encoding the VH and VL chain may be converted to full-length antibody genes by inserting them into expression vectors already encoding heavy chain constant and light chain constant regions, respectively, such that the VH segment is operatively linked to the heavy chain constant region (CH) segment(s) within the vector and the VL segment is operatively linked to the light chain constant region (CL) segment within the vector. Alternatively, the nucleic acid molecules encoding the VH or VL chains are converted into full-length antibody genes by linking, e.g., ligating, the nucleic acid molecule encoding a VH chain to a nucleic acid molecule encoding a CH chain using standard molecular biological techniques. The same may be achieved using nucleic acid molecules encoding VL and CL chains. The sequences of human heavy and light chain constant region genes are known in the art. See, e.g., Kabat et al., Sequences of Proteins of Immunological Interest, 5th Ed., NIH Publ. No. 91-3242, 1991. Nucleic acid molecules encoding the full-length heavy and/or light chains may then be expressed from a cell into which they have been introduced and the OX40R antibody isolated.

The nucleic acid molecules may be used to recombinantly express large quantities of OX40R antibodies, as described below. The nucleic acid molecules may also be used to produce other binding molecules provided by the disclosure, such as chimeric antibodies, single chain antibodies, immunoadhesins, diabodies, mutated antibodies, and antibody derivatives, as described elsewhere herein. In one embodiment, a nucleic acid molecule is used as probe or PCR primer for specific antibody sequences. For instance, a nucleic acid molecule probe may be used in diagnostic methods or a nucleic acid molecule PCR primer may be used to amplify regions of DNA that could be used, inter alia, to isolate nucleic acid sequences for use in producing variable regions of the OX40R antibodies.

Once DNA molecules encoding the $V_H$ and $V_L$ segments of an OX40R antibody are obtained, these DNA molecules can be further manipulated by recombinant DNA techniques, for example to convert the variable region genes to full-length antibody chain genes, to Fab fragment genes, or to a scFv gene. In these manipulations, a $V_L$- or $V_H$-encoding DNA molecule is operatively linked to another DNA molecule encoding another polypeptide, such as an antibody constant region or a flexible linker. The term "operatively linked," as used in this context, means that the two DNA molecules are joined such that the amino acid sequences encoded by the two DNA molecules remain in-frame.

The isolated DNA molecule encoding the $V_H$ region can be converted to a full-length heavy chain gene by operatively linking the $V_H$-encoding DNA molecule to another DNA molecule encoding heavy chain constant regions (CH1, CH2 and CH3). The sequences of human heavy chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG2 constant region. The IgG1 constant region sequence can be any of the various alleles or allotypes known to occur among different individuals, such as Gm(1), Gm(2), Gm(3), and Gm(17). These allotypes represent naturally occurring amino acid substitutions in the IgG1 constant regions. For a Fab fragment heavy chain gene, the $V_H$-encoding DNA can be operatively linked to another DNA molecule encoding only the heavy chain CH1 constant region. The CH1 heavy chain constant region may be derived from any of the heavy chain genes.

The isolated DNA molecule encoding the $V_L$ region can be converted to a full-length light chain gene (as well as a Fab light chain gene) by operatively linking the $V_L$-encoding DNA molecule to another DNA molecule encoding the light chain constant region, $C_L$. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the $V_H$- and $V_L$-encoding DNA fragments are operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ regions joined by the flexible linker (See e.g., Bird et al., (1988) Science 242:423-426; Huston et al., (1988) Proc. Natl. Acad. Sci. USA 85:5879-5883; McCafferty et al., (1990) Nature 348:552-554). The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to OX40R and to another molecule.

In another aspect, the present disclosure provides a vector, which comprises a nucleic acid molecule described herein above. The nucleic acid molecule may encode a portion of a light chain or heavy chain (such as a CDR or a variable region), a full-length light or heavy chain, polypeptide that comprises a portion or full-length of a heavy or light chain, or an amino acid sequence of an antibody derivative or antigen binding fragment. To express a binding molecule, a DNA molecule encoding partial or full-length binding molecule is inserted into an expression vector such that the DNA molecule is operatively linked to transcriptional and translational control sequences. In this context, the term "operatively linked" is intended to mean that the DNA molecule is ligated into a vector such that transcriptional and translational control sequences within the vector serve their intended function of regulating the transcription and translation of the DNA molecule. The expression vector and expression control sequences are chosen to be compatible with the expression host cell used. Expression vectors include, for example, plasmids, retroviruses, adenoviruses, adeno-associated viruses (AAV), plant viruses such as cauliflower mosaic virus, tobacco mosaic virus, cosmids, YACs, and EBV derived episomes. The DNA molecule encoding an amino acid sequence of the light chain and DNA molecule encoding an amino acid sequence of the heavy chain can be inserted into separate vectors or in the same vector. The DNA molecule is inserted into the expression vector by any suitable methods (e.g., ligation of complementary restriction sites on the antibody gene fragment and vector, or blunt end ligation if no restriction sites are present).

An example of a suitable expression vector is one that encodes a functionally complete human $C_H$ or $C_L$ immunoglobulin sequence, with appropriate restriction sites engineered so that any $V_H$ or $V_L$ sequence can be inserted and expressed. The expression vector also can encode a signal peptide that facilitates secretion of the amino acid sequence of the antibody chain from a host cell. The DNA encoding the amino acid sequence of an antibody chain may be cloned into the vector such that the signal peptide is linked in-frame to the amino terminus of the amino acid sequence of the antibody chain. The signal peptide can be an immunoglobulin signal peptide or a heterologous signal peptide (i.e., a signal peptide from a non-immunoglobulin protein).

In addition to the nucleic acid sequence encoding an amino acid sequence of an OX40R antibody (antibody chain genes), the expression vectors carry regulatory sequences that control the expression of the antibody chain genes in a host cell. The design of the expression vector, including the selection of regulatory sequences, may depend on such factors as the choice of the host cell to be transformed, the level of expression of protein desired, and so forth. Regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245, and 4,968,615.

In addition to the antibody chain nucleic acid sequences and regulatory sequences, the recombinant expression vectors may carry additional sequences, such as sequences that regulate replication of the vector in host cells and selectable marker genes. The selectable marker gene facilitates selection of host cells into which the vector has been introduced (see e.g., U.S. Pat. Nos. 4,399,216, 4,634,665 and 5,179,017). Selectable marker genes include the dihydrofolate reductase (DHFR) gene (for use in dhfr-host cells with methotrexate selection/amplification), the neomycin phosphotransferase gene (for G418 selection), and the glutamate synthetase gene. The design of the expression vector, including the selection of regulatory sequences, may depend on a number of factors, such as the choice of the host cell to be transformed, the level of expression of protein desired, and so forth. Nucleic acid molecules encoding binding molecules and vectors comprising these nucleic acid molecules can be used for transformation of a suitable host cell for recombinant production of a binding molecule. A suitable host cell is transformed with one or more expression vectors carrying nucleic acid molecules encoding an amino acid sequence of a binding molecule such that the amino acid sequence is expressed in the host cell and, typically, secreted into the medium in which the host cell is cultured and from which medium the amino acid sequence can be recovered. Transformation of host cells can be by carried out by any suitable method know in the art, such as those disclosed in U.S. Pat. Nos. 4,399,216, 4,912,040, 4,740,461, and 4,959,455.

The host cell may be a mammalian, insect, plant, bacterial, or yeast cell. Examples of mammalian cell lines suitable as host cells include Chinese hamster ovary (CHO) cells, NS0 cells, SP2 cells, HEK-293T cells, NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Examples of insect cell lines include Sf9 or Sf21 cells. Examples of plant host cells include *Nicotiana, Arabidopsis*, duckweed, corn, wheat, potato, and so forth. Bacterial host cells include *E. coli* and *Streptomyces* species. Examples of yeast host cells include *Schizosaccharomyces pombe, Saccharomyces cerevisiae*, and *Pichia pastoris*.

Amino acid sequences of a binding molecule expressed by different cell lines or in transgenic animals may have different glycosylation. However, all binding molecules encoded by the nucleic acid molecules provided herein, or comprising the amino acid sequences provided herein are part of the present invention, regardless of the glycosylation of the binding molecules.

In another aspect, the present disclosure provides a method for producing an OX40R antibody or antigen-binding fragment thereof using phage display. The method comprises (a) synthesizing a library of human antibodies on phage, (b) screening the library with the OX40R or a portion thereof, (c) isolating phage that binds the OX40R or a portion thereof, and (d) obtaining the antibody from the phage. One exemplary method for preparing the library of antibodies comprises the step of: (a) immunizing a non-human animal comprising human immunoglobulin loci with OX40R or an antigenic portion thereof to create an immune response; (b) extracting antibody-producing cells from the immunized animal; (c) isolating RNA encoding heavy and light chains of the OX40R antibodies from the extracted cells; (d) reverse transcribing the RNA to produce cDNA; (e), amplifying the cDNA; and (f) inserting the cDNA into a phage display vector such that antibodies are expressed on the phage. Recombinant human OX40R antibodies or antigen binding fragments thereof can be isolated by screening a recombinant combinatorial antibody library. The library may be a scFv phage display library, generated using human $V_L$ and $V_H$ cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612).

In one case, to isolate and produce human OX40R antibodies with the desired characteristics, a human OX40R antibody as described herein is first used to select human heavy and light chain sequences having similar binding activity toward OX40R using methods known in the art, such as the epitope imprinting methods described in WO 93/06213. The antibody libraries used in this method may be scFv libraries prepared and screened as described in WO 92/01047, McCafferty et al., Nature 348:552-554 (1990); and Griffiths et al., EMBO J. 12:725-734 (1993). The scFv antibody libraries may be screened using human CCR2 as the antigen.

Once initial human $V_L$ and $V_H$ regions are selected, "mix and match" experiments are performed, in which different pairs of the initially selected $V_L$ and $V_H$ segments are screened for OX40R binding to select $V_L/V_H$ pair combinations. Additionally, to further improve the quality of the antibody, the $V_L$ and $V_H$ segments of the $V_L/V_H$ pair(s) can be randomly mutated, within the CDR3 region of $V_H$ and/or $V_L$, in a process analogous to the in vivo somatic mutation process responsible for affinity maturation of antibodies during a natural immune response. This in vitro affinity maturation can be accomplished by amplifying $V_H$ and $V_L$ domains using PCR primers complimentary to the $V_H$ CDR3 or $V_L$ CDR3, respectively, which primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be re-screened for binding to OX40R.

Following screening and isolation of an OX40R antibody or antigen binding portion from a recombinant immunoglobulin display library, nucleic acids encoding the selected binding molecule can be recovered from the display package (e.g., from the phage genome) and subcloned into other expression vectors by recombinant DNA techniques. If desired, the nucleic acid can further be manipulated to create other antibody forms, as described below. To express a recombinant human antibody isolated by screening of a combinatorial library, the DNA encoding the antibody is cloned into a recombinant expression vector and introduced into mammalian host cells, as described above.

Pharmaceutical Compositions

In another aspect, the present disclosure provides a composition, e.g., a pharmaceutical composition, containing one or a combination of binding molecules provided by the disclosure, and optionally a pharmaceutically acceptable carrier. The compositions can be prepared by conventional methods known in the art.

In some embodiments, the composition comprises an OX40R antibody or an antigen-binding fragment thereof. In a particular embodiment, the composition comprises antibody 11D4 or antibody 18D8, or a antigen-binding fragment of either antibody. In still other embodiments, the composition comprises a derivative of antibody 11D4 or antibody 18D8.

The term "pharmaceutically acceptable carrier" refers to any inactive substance that is suitable for use in a formulation for the delivery of a binding molecule. A carrier may be an antiadherent, binder, coating, disintegrant, filler or diluent, preservative (such as antioxidant, antibacterial, or antifungal agent), sweetener, absorption delaying agent, wetting agent, emulsifying agent, buffer, and the like. Examples of suitable pharmaceutically acceptable carriers include water, ethanol, polyols (such as glycerol, propylene glycol, polyethylene glycol, and the like) dextrose, vegetable oils (such as olive oil), saline, buffer, buffered saline, and isotonic agents such as sugars, polyalcohols, sorbitol, and sodium chloride.

The compositions may be in any suitable forms, such as liquid, semi-solid, and solid dosage forms. Examples of liquid dosage forms include solution (e.g., injectable and infusible solutions), microemulsion, liposome, dispersion, or suspension. Examples of solid dosage forms include tablet, pill, capsule, microcapsule, and powder. A particular form of the composition suitable for delivering a binding molecule is a sterile liquid, such as a solution, suspension, or dispersion, for injection or infusion. Sterile solutions can be prepared by incorporating the antibody in the required amount in an appropriate carrier, followed by sterilization microfiltration. Generally, dispersions are prepared by incorporating the antibody into a sterile vehicle that contains a basic dispersion medium and other carriers. In the case of sterile powders for the preparation of sterile liquid, methods of preparation include vacuum drying and freeze-drying (lyophilization) to yield a powder of the active ingredient plus any additional desired ingredient from a previously sterile-filtered solution thereof. The various dosage forms of the compositions can be prepared by conventional techniques known in the art.

The relative amount of a binding molecule included in the composition will vary depending upon a number of factors, such as the specific binding molecule and carriers used, dosage form, and desired release and pharmacodynamic characteristics. The amount of a binding molecule in a single dosage form will generally be that amount which produces a therapeutic effect, but may also be a lesser amount. Generally, tins amount will range from about 0.01 percent to about 99 percent, from about 0.1 percent to about 70 percent, or from about 1 percent to about 30 percent relative to the total weight of the dosage form.

In addition to the binding molecule, one or more additional therapeutic agents may be included in the composition. Examples of the additional therapeutic agents are described herein below. The suitable amount of the additional therapeutic agent to be included in the composition can be readily selected by a person skilled in the art, and will vary depending on a number of factors, such as the particular agent and carriers used, dosage form, and desired release and pharmacodynamic characteristics. The amount of the additional therapeutic agent included in a single dosage form will generally be that amount of the agent which produces a therapeutic effect, but may be a lesser amount as well.

Use of the Binding Molecules and Pharmaceutical Compositions

Binding molecules and pharmaceutical compositions comprising a binding molecule provided by the present disclosure are useful for therapeutic, diagnostic, or other purposes, such as enhancing an immune response, treating cancer, enhancing efficacy of other cancer therapy, or enhancing vaccine efficacy, and have a number of utilities, such as for use as medicaments or diagnostic agents. Thus, in another aspect, the present disclosure provides methods of using the binding molecules or pharmaceutical compositions.

In one particular aspect, methods are provided for enhancing immune response in a mammal, comprising administering to the mammal a therapeutically effective amount of a binding molecule provided by the disclosure. In some embodiments, the binding molecule is an OX40R antibody or antigen-binding fragment thereof and the mammal is a human. In a further embodiment, the binding molecule is antibody 11D4 or antibody 18D8, or an antigen-binding fragment of either antibody. The term "enhancing immune response" or its grammatical variations, means stimulating, evoking, increasing, improving, or augmenting any response of a mammal's immune system. The immune response may be a cellular response (i.e. cell-mediated, such as cytotoxic T lymphocyte mediated) or a humoral response (i.e. antibody mediated response), and may be a primary or secondary immune response. Examples of enhancement of immune response include increased CD4+ helper T cell activity and generation of cytolytic T cells. The enhancement of immune response can be assessed using a number of in vitro or in vivo measurements known to those skilled in the art, including, but not limited to, cytotoxic T lymphocyte assays, release of cytokines (for example IL-2 production), regression of tumors, survival of tumor bearing animals, antibody production, immune cell proliferation, expression of cell surface markers, and cytotoxicity. Typically, methods of the disclosure enhance the immune response by a mammal when compared to the immune response by an untreated mammal or an animal not treated using the claimed methods. In one embodiment, the method enhances a cellular immune response, particularly a cytotoxic T cell response. In another embodiment, the cellular immune response is a T helper cell response. In still another embodiment, the immune response is a cytokine production, particularly IL-2 production.

In another particular aspect, the present disclosure provides a method of treating cancer in a mammal, comprising administering to the mammal a therapeutically effective amount of a binding molecule provided by the disclosure. The term "treating cancer" or "treatment of cancer" refers to causing a desirable or beneficial effect in a mammal diagnosed with a cancer. The desirable or beneficial effect may include inhibition of further growth or spread of cancer cells, death of cancer cells, inhibition of reoccurrence of cancer, reduction of pain associated with the cancer, or improved survival of the animal. Inhibition of reoccurrence of cancer contemplates cancer sites and surrounding tissue which have previously been treated by radiation, chemotherapy, surgery, or other techniques. The effect can be either subjective or objective. For example, if the animal is human, the human may note improved vigor or vitality or decreased pain as subjective symptoms of improvement or response to therapy. Alternatively, the clinician may notice a decrease in tumor size or tumor burden based on physical exam, laboratory parameters, tumor markers or radiographic findings. Some laboratory signs that the clinician may observe for response to treatment include normalization of tests, such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement, such as sonograms, nuclear magnetic resonance testing and positron emissions testing. In some embodiments, the binding molecule is an OX40R antibody or an antigen-binding fragment thereof provided by the disclosure. In a further embodiment the binding molecule is antibody 11D4 or 18D8, or an antigen-binding fragment of either antibody. In a further embodiment, the mammal is a human.

In another particular aspect, the present disclosure provides a method of preventing cancer in a mammal, comprising administering to the mammal a therapeutically effective amount of a binding molecule provided by the disclosure. The term "preventing cancer" or "prevention of cancer" refers to delaying, inhibiting, or preventing the onset of a cancer in a mammal in which the onset of oncogenesis or tumorigenesis is not evidenced but a predisposition for cancer is identified whether determined by genetic screening, for example, or otherwise. The term also encompasses treating a mammal having premalignant conditions to stop the progression of, or cause regression of, the premalignant conditions towards malignancy. Examples of premalignant conditions include hyperplasia, dysplasia, and metaplasia. In some embodiments, the binding molecule is an OX40R antibody or a fragment thereof provided by the disclosure. In a further embodiment the binding molecule is antibody 11D4 or 18D8, or an antigen-binding fragment of either antibody. In a further embodiment, the mammal is a human.

A variety of cancers, whether malignant or benign and whether primary or secondary, may be treated or prevented with a method provided by the disclosure. Examples of such cancers include lung cancers such as bronchogenic carcinoma (e.g., squamous cell carcinoma, small cell carcinoma, large cell carcinoma, and adenocarcinoma), alveolar cell carcinoma, bronchial adenoma, chondromatous hamartoma (noncancerous), and sarcoma (cancerous); heart cancer such as myxoma, fibromas, and rhabdomyomas; bone cancers such as osteochondromas, condromas, chondroblastomas, chondromyxoid fibromas, osteoid osteomas, giant cell tumors, chondrosarcoma, multiple myeloma, osteosarcoma, fibrosarcomas, malignant fibrous histiocytomas, Ewing's tumor (Ewing's sarcoma), and reticulum cell sarcoma; brain cancer such as gliomas (e.g., glioblastoma multiforme), anaplastic astrocytomas, astrocytomas, oligodendrogliomas, medulloblastomas, chordoma, Schwannomas, ependymomas, meningiomas, pituitary adenoma, pinealoma, osteomas, hemangioblastomas, craniopharyngiomas, chordomas, germinomas, teratomas, dermoid cysts, and angiomas; cancers in digestive system such as leiomyoma, epidermoid carcinoma, adenocarcinoma, leiomyosarcoma, stomach adenocarcinomas, intestinal lipomas, intestinal neurofibromas, intestinal fibromas, polyps in large intestine, and colorectal cancers; liver cancers such as hepatocellular adenomas, hemangioma, hepatocellular carcinoma, fibrolamellar carcinoma, cholangiocarcinoma, hepatoblastoma, and angiosarcoma; kidney cancers such as kidney adenocarcinoma, renal cell carcinoma, hypernephroma, and transitional cell carcinoma of the renal pelvis; bladder cancers; hematological cancers such as acute lymphocytic (lymphoblastic) leukemia, acute myeloid (myelocytic, myelogenous, myeloblastic, myelomonocytic) leukemia, chronic lymphocytic leukemia (e.g., Sezary syndrome and hairy cell leukemia), chronic myelocytic (myeloid, myelogenous, granulocytic) leukemia, Hodgkin's lymphoma, non-Hodgkin's lymphoma, B cell lymphoma, mycosis fungoides, and myeloproliferative disorders (including myeloproliferative disorders such as polycythemia vera, myelofibrosis, thrombocythemia, and chronic myelocytic leukemia); skin cancers such as basal cell carcinoma, squamous cell carcinoma, melanoma, Kaposi's sarcoma, and Paget's disease; head and neck cancers; eye-related cancers such as retinoblastoma and intraoccular melanocarcinoma; male reproductive system cancers such as benign prostatic hyperplasia, prostate cancer, and testicular cancers (e.g., seminoma, teratoma, embryonal carcinoma, and choriocarcinoma); breast cancer; female reproductive system cancers such as uterine cancer (endometrial carcinoma), cervical cancer (cervical carcinoma), cancer of the ovaries (ovarian carcinoma), vulvar carcinoma, vaginal carcinoma, fallopian tube cancer, and hydatidiform mole; thyroid cancer (including papillary, follicular, anaplastic, or medullary cancer); pheochromocytomas (adrenal gland); noncancerous growths of the parathyroid glands; pancreatic cancers; and hematological cancers such as leukemias, myelomas, non-Hodgkin's lymphomas, and Hodgkin's lymphomas.

In practicing the therapeutic methods, the binding molecules may be administered alone us monotherapy, or administered in combination with one or more additional therapeutic agents or therapies. Thus, in another aspect, the present disclosure provides a combination therapy, which comprises a binding molecule provided by the disclosure in combination with one or more additional therapies or therapeutic agents. The term "additional therapy" refers to a therapy which does not employ a binding molecule provided by the disclosure as a therapeutic agent. The term "additional therapeutic agent" refers to any therapeutic agent other than a binding molecule provided by the disclosure. In some embodiments, the binding molecule is antibody 11D4 or 18D8, or an antigen-binding fragment of either antibody. In one particular aspect, the present disclosure provides a combination therapy for treating cancer in a mammal, which comprises administering to the mammal a therapeutically effective amount of a binding molecule provided by the disclosure in combination with one or more additional therapeutic agents. In a further embodiment, the mammal is a human.

A wide variety of cancer therapeutic agents may be used in combination with a binding molecule. One of ordinary skill in the art will recognize the presence and development of other cancer therapies which can be used in combination with the methods and binding molecules of the present disclosure, and will not be restricted to those forms of therapy set forth herein. Examples of categories of additional therapeutic agents that may be used in the combination therapy for treating cancer include (1) chemotherapeutic agents, (2) immunotherapeutic agents, and (3) hormone therapeutic agents.

The term "chemotherapeutic agent" refers to a chemical or biological substance that can cause death of cancer cells, or interfere with growth, division, repair, and/or function of cancer cells. Examples of chemotherapeutic agents include those that are disclosed in WO 2006/088639, WO 2006/129163, and US 20060153808, the disclosures of which are incorporated herein by reference. Examples of particular chemotherapeutic agents include: (1) alkylating agents, such as chlorambucil (LEUKERAN), mcyclophosphamide (CYTOXAN), ifosfamide (IFEX), mechlorethamine hydrochloride (MUSTARGEN), thiotepa (THIOPLEX), streptozotocin (ZANOSAR), carmustine (BICNU, GLIADEL WAFER), lomustine (CEENU), and dacarbazine (DTIC-DOME); (2) alkaloids or plant vinca alkaloids, including cytotoxic antibiotics, such as doxorubicin (ADRIAMYCIN), epirubicin (ELLENCE, PHARMORUBICIN), daunorubicin (CERUBIDINE, DAUNOXOME), nemorubicin, idarubicin (IDAMYCIN PFS, ZAVEDOS), mitoxantrone (DHAD, NOVANTRONE), dactinomycin (actinomycin D, COSMEGEN), plicamycin (MITHRACIN), mitomycin (MUTAMYCIN), and bleomycin (BLENOXANE), vinorelbine tartrate (NAVELBINE)), vinblastine (VELBAN), vincristine (ONCOVIN), and vindesine (ELDISINE); (3) antimetabolites, such as capecitabine (XELODA), cytarabine (CYTOSAR-U), fludarabine (FLUDARA), gemcitabine (GEMZAR), hydroxyurea (HYDRA), methotrexate (FOLEX, MEXATE, TREXALL), nelarabine (ARRANON), trimetrexate (NEUTREXIN), and pemetrexed (ALIMTA); (4) Pyrimidine antagonists, such as 5-fluorouracil (5-FU); capecitabine (XELODA), raltitrexed (TOMUDEX), tegafur-uracil (UFTORAL), and gemcitabine (GEMZAR); (5) taxanes, such as docetaxel (TAXOTERE), paclitaxel (TAXOL); (6) platinum drugs, such as cisplatin (PLATINOL) and carboplatin (PARAPLATIN), and oxaliplatin (ELOXATIN); (7) topoisomerase inhibitors, such as irinotecan (CAMPTOSAR), topotecan (HYCAMTIN), etoposide (ETOPOPHOS, VEPESSID, TOPOSAR), and teniposide (VUMON); (8) epipodophyllotoxins (podophyllotoxin derivatives), such as etoposide (ETOPOPHOS, VEPESSID, TOPOSAR); (9) folic acid derivatives, such as leucovorin (WELLCOVORIN); (10) nitrosoureas, such as carmustine (BiCNU), lomustine (CeeNU); (11) inhibitors of receptor tyrosine kinase, including epidermal growth factor receptor (EGFR), vascular endothelial growth factor (VEGF), insulin receptor, insulin-like growth factor receptor (IGFR), hepatocyte growth factor receptor (HGFR), and platelet-derived growth factor receptor (PDGFR), such as gefitinib (IRESSA), erlotinib (TARCEVA), bortezomib (VELCADE), imatinib mesylate (GLEEVEC), genefitinib, lapatinib, sorafenib, thalidomide, sunitinib (SUTENT), axitinib, rituximab, trastuzumab (HERCEPTIN), cetuximab (ERBITUX), bevacizumab (AVASTIN), and ranibizumab (LUCENTIS), lym-1 (ONCOLYM), antibodies to insulin-like growth factor-1 receptor (IGF-1R) that are disclosed in WO2002/053596); (12) angiogenesis inhibitors, such as bevacizumab (AVASTIN), suramin (GERMANIN), angiostatin, SU5416, thalidomide, and matrix metalloproteinase inhibitors (such as batimastat and marimastat), and those that are disclosed in WO2002055106; and (13) proteasome inhibitors, such as bortezomib (VELCADE).

The term "immunotherapeutic agents" refers to a chemical or biological substance that can enhance an immune response of a mammal. Examples of immunotherapeutic agents include: *bacillus* Calmette-Guerin (BCG); cytokines such as interferons; vaccines such as MyVax personalized immunotherapy; Onyvax-P, Oncophage, GRNVAC1, FavId, Provenge, GVAX, Lovaxin C, BiovaxID, GMXX, and NeuVax; and antibodies such as alemtuzumab (CAMPATH), bevacizumab (AVASTIN), cetuximab (ERBITUX), gemtuzunab ozogamicin (MYLOTARG), ibritumomab tiuxetan (ZEVALIN), panitumumab (VECTIBIX), rituximab (RITUXAN, MABTHERA), trastuzumab (HERCEPTIN), tositumomab (BEXXAR), tremelimumab, CAT-3888, and agonist antibodies to CD40 receptor that are disclosed in WO2003/040170.

The term "hormone therapeutic agent" refers to a chemical or biological substance that inhibits or eliminates the production of a hormone, or inhibits or counteracts the effect of a hormone on the growth and/or survival of cancerous cells. Examples of such agents suitable for the methods herein include those that are disclosed in US20070117809. Examples of particular hormone therapeutic agents include tamoxifen (NOLVADEX), toremifene (Fareston), fulvestrant (FASLODEX), anastrozole (ARIMIDEX), exemestane (AROMASIN), letrozole (FEMARA), megestrol acetate (MEGACE), goserelin (ZOLADEX), and leuprolide (LUPRON). The binding molecules of this disclosure may also be used in combination with non-drug hormone therapies such as (1) surgical methods that remove all or part of the organs or glands which participate in the production of the hormone, such as the ovaries, the testicles, the adrenal gland, and the pituitary gland, and (2) radiation treatment, in which the organs or glands of the patient are subjected to radiation in an amount sufficient to inhibit or eliminate the production of the targeted hormone.

The combination therapy for treating cancer also encompasses the combination of a binding molecule provided by the disclosure with surgery to remove a tumor. The binding molecule may be administered to the mammal before, during, or after the surgery.

The combination therapy for treating cancer also encompasses combination of a binding molecule provided by the disclosure with radiation therapy, such as ionizing (electromagnetic) radiotherapy (e.g., X-rays or gamma rays) and particle beam radiation therapy (e.g., high linear energy radiation). The source of radiation can be external or internal to the mammal. The binding molecule may be administered to the mammal before, during, or after the radiation therapy.

Administration of the Binding Molecules and Compositions

The binding molecules and compositions provided by the present disclosure can be administered via any suitable enteral route or parenteral route of administration. The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. Examples of parenteral routes of administration include intravenous, intramuscular, intradermal, intraperitoneal, intratumor, intravesical, intraarterial, intrathecal, intracapsular, intraorbital, intracardiac, transtracheal, intraarticular, subcapsular, subarachnoid, intraspinal, epidural and intrasternal, subcutaneous, or topical administration. The antibodies and compositions of die disclosure can be administered using any suitable method, such as by oral ingestion, nasogastric tube, gastrostomy tube, injection, infusion, implantable infusion pump, and osmotic pump. The suitable route and method of administration may vary depending on a number of factors such as the specific antibody being used, the rate of absorption desired, specific formulation or dosage form used, type or severity of the disorder being treated, the specific site of action, and conditions of the patient, and can be readily selected by a person skilled in the art The term "therapeutically effective amount" of a binding molecule refers to an amount that is effective for an intended therapeutic purpose. For example, in the context of enhancing an immune response, a "therapeutically effective amount" is any amount that is effective in stimulating, evoking, increasing, improving, or augmenting any response of a mammal's immune system. In the context of treating cancer, a "therapeutically effective amount" is any amount that is sufficient to cause any desirable or beneficial effect in the mammal being treated, such as inhibition of further growth or spread of cancer cells, death of cancer cells, inhibition of reoccurrence of cancer, reduction of pain associated with the cancer, or improved survival of the mammal. In a method of preventing cancer, a "therapeutically effective amount" is any amount that is effective in delaying, inhibiting, or preventing the onset of a cancer in the mammal to which the binding molecule is administered. The therapeutically effective amount of a binding molecule usually ranges from about 0.001 to about 500 mg/kg, and more usually about 0.05 to about 100 mg/kg, of the body weight of the mammal. For example, the amount can be about 0.3 mg/kg, 1 mg/kg, 3 mg/kg, 5 mg/kg, 10 mg/kg, 50 mg/kg, or 100 mg/kg of body weight of the mammal. In some embodiments, the therapeutically effective amount of an OX40R antibody is in the range of about 0.1-30 mg/kg of body weight of the mammal. The precise dosage level to be administered can be readily determined by a person skilled in the art and will depend on a number of factors, such as the type, and severity of the disorder to be treated, the particular binding molecule employed, the route of administration, the time of administration, the duration of the treatment, the particular additional therapy employed, the age, sex, weight, condition, general health and prior medical history of the patient being treated, and like factors well known in the medical arts.

A binding molecule or composition is usually administered on multiple occasions. Intervals between single doses can be, for example, weekly, monthly, every three months or yearly. An exemplary treatment regimen entails administration once per week, once every two weeks, once every three weeks, once every four weeks, once a month, once every 3 months or once every three to 6 months. Typical dosage regimens for an OX40R antibody include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks.

EXAMPLES

Example 1: Preparation of OX40R Antibodies

Illustrative antibodies in accordance with the disclosure were prepared, selected, and assayed as follows:

Immunization with the OX40R Antigen and Selection of Mice Producing OX40R Monoclonal Antibodies:

Fully human monoclonal antibodies to human OX40R were prepared using human Ig transgenic mouse strains HCo7, HCo12, Hco17, and Hco27 as well as the human transchromosomal/transgenic strain, KM (Medarex, Inc.). These strains all express fully human antibodies that are indistinguishable from antibodies isolated from humans.

In the transgenic strains, both the endogenous mouse kappa light chain gene and the endogenous mouse heavy chain gene were homozygously disrupted as described in Chen et al. (1993) EMBO J. 12:821-830 and in Example 1 of WO 01/09187, respectively. Moreover, they carry a human kappa light chain transgene, KCo5, as described in Fishwild et al. (1996) Nature Biotechnology 14:845-851. In contrast, the transgenic strains are distinct with respect to their human heavy chain genes. The HCo7 strain carries the HCo7 human heavy chain transgene as described in U.S. Pat. Nos. 5,545,806, 5,625,825, and 5,545,807; the HCo12 strain carries the HCo12 human heavy chain transgene as described in Example 2 of WO 01/09187; the Hco17 strain carries the Hco17 human heavy chain transgene as described in Example 8 of Deshpande et al., US 2005/0191293A1; the Hco27 strain carries the Hco27 human heavy chain transgene as described in Example 5 of PCT/US2008/072640 filed 8 Aug. 2008. The KM strain carries a human minichromosome as described in Ishida et al., (2002), Cloning and Stem Cells, 4: 91-102.

General immunization schemes for HuMab mice are described in Lonberg et al. (1994) Nature 368(6474): 856-859; Fishwild et al. (1996) Nature Biotechnology 14: 845-851; and PCT Publication WO 98/24884.

HuMab mice of the HCo7, HCo12, Hco17, Hco27 and KM strains were immunized beginning at 6-16 weeks of age with 15-25 µgs of purified human recombinant OX40R-Ig protein and murine pre-B cell line, 300-19 (Reth, M. G. et al., Nature 312 29: 418-42, 1984; Alt, F. et al., Cell 27: 381-390, 1981), transfected to express human OX40R in Ribi adjuvant. The purified human recombinant OX40R-Ig protein is a construct of the extracellular domain (amino acids 1-220) of human OX40R fused to the constant region of human IgG1. Administration was via injection intraperitoneally, subcutaneously or into the footpad at 3-28 day intervals, up to a total of 10 immunizations. Immune response was monitored via ELISA and FACS screening as described below.

Selection of HuMab Mice Producing OX40R Antibodies:

To select HuMab mice producing antibodies that bind to the OX40R, blood from the immunized mice was obtained and analyzed by ELISA for specific binding to purified human OX40R recombinant protein, and by FACS for binding to a cell line expressing full length human OX40R, and not to a control cell line not expressing OX40R.

ELISA binding assay was as described by Fishwild et al. (1996), Nature Biotechnology 14: 845-851. Briefly, microtiter plates were coated using 50 µl/well of a purified recombinant OX40R-Ig solution containing 1 µg/ml in PBS, and incubated overnight at 4° C. The wells were then blocked using 200 µl/well of 5% chicken serum in PBS/Tween (0.05%). Dilutions of plasma from OX40R-immunized mice were added to each well and incubated for 1 hour at ambient temperature. The plates were washed with PBS/Tween and then incubated with a goat-anti-human IgG Fc polyclonal antibody conjugated with horseradish peroxidase (HRP) for 1 hour at room temperature. After washing, the plates were developed with ABTS substrate (Moss Inc., product #: ABTS-1000 mg/ml) and analyzed by spectrophotometer at OD 405.

FACS assay was carried out according to conventional procedures. Briefly, OX40R-expressing 300-19 cells were incubated with serum from immunized mice diluted at 1:20. Cells were washed and specific antibody binding was detected with FITC-labeled anti-human IgG Ab. Flow cytometric analyses were performed on a FACS flow cytometry instrument (Becton Dickinson, San Jose, Calif.).

Mice that developed the highest titers of OX40R antibodies were used for fusions. Fusions were performed as described below and hybridoma supernatants were tested for anti-OX40R activity by ELISA and FACS.

Generation of Hybridomas Producing Human Monoclonal Antibodies to OX40R:

The mice selected above were boosted intravenously with OX40R-Ig at 3 days and then again at 2 days prior to sacrifice and removal of the spleen and/or lymph nodes.

The splenocytes and/or lymph node lymphocytes isolated from the immunized HuMab or KM mice were fused to SP2/0 non-secreting mouse myeloma cells (ATCC, CRL-1581) using electrofusion (E-fusion, Cyto Pulse™ technology, Cyto Pulse™ Sciences, Inc., Glen Burnie, Md.), according to standard or manufacturer-recommended protocols. Briefly, single cell suspensions of splenocytes and/or lymph node lymphocytes from immunized mice were prepared and then combined with an equal number of SP2/0 non-secreting mouse myeloma cells; E-fusion was then performed.

The cells were then plated at $2 \times 10^4$ cells/well in flat bottom microtiter plate, and incubated for 10-14 days in selective medium containing 10% fetal bovine serum, 10% P388D1 (ATCC, CRL-TIB-63) conditioned medium, 3-5% (IGEN) in DMEM (Mediatech, Herndon, Va., Cat. No. CRL 10013, with high glucose, L-glutamine and sodium pyruvate), 7 mM HEPES, 0.055 mM 2-mercaptoethanol, 0.1 IU/mL penicillin-0.1 mg/mL streptomycin, and 1×HAT (Sigma, Cat. No. CRL-P-7185).

After 1-2 weeks, cells were cultured in medium in which the HAT was replaced with HT. Approximately 10-14 days after cell plating, supernatants from individual wells were screened for the presence of human gamma, kappa antibodies. The supernatants which scored positive for human gamma, kappa were then screened by ELISA and FACS (using the protocol described above) for human OX40R monoclonal IgG antibodies. The antibody-secreting hybridomas were transferred to 24 well plates, screened again and, if confirmed positive for human OX40R IgG monoclonal antibodies, were subcloned at least twice by limiting dilution. The stable subclones were then cultured in vitro to generate small amounts of antibody in tissue culture medium for further characterization.

Example 2: Biological/Pharmacological Examples

A. In Vitro Study Procedures:

Binding to the Extracellular Domain of the OX40R: A human OX40-Ig fusion protein was diluted in BupH™ Carbonate buffer, pH 9.4 (Pierce, Rockford, Ill.) was coated onto 96-well Maxisorb plates (Nunc, Roskilde, Denmark) at 100 µl/well (0.25 µg/ml) and incubated overnight at 4° C. The Plates were washed three times with wash buffer containing 0.05% Tween 20 (Sigma, St Louis, Mo.) diluted in PBS (Sigma, St Louis, Mo.) and blocked with 300 µl/well of 0.5% BSA (Sigma, St Louis, Mo.) in PBS for 1 hour at RT °. Next, the plates were washed and incubated with anti-human OX40 reactive antibodies diluted in blocking buffer at various concentrations (100 µl/well) and incubated for 1 hour at RT °. The plates were then washed and incubated for one hour at RT ° with a horse radish peroxidase labeled anti-human kappa chain antibody (Bethyl Laboratories, Montgomery, Tex.) at 25 ng/ml in blocking buffer. Finally, the assay plates were washed and 100 µl/well of 1-Step Turbo-TMB substrate (Pierce, Rockford, Ill.) was added for 30 minutes at RT °. The reaction was stopped by adding an equal volume of 2M $H_2SO_4$ and absorbance was read at 450 nm on a Molecular Devices Spectra Max 340 (Molecular Devices, Sunnyvale, Calif.).

FACS Based Binding to Cell Surface OX40R:

OX40R-expressing cell lines (see below) or activated primary peripheral blood mononuclear cells (see below) were used to assess binding on both the human and cynomolgus OX40 receptors. Cells were harvested and washed ($5 \times 10^5$/tube) using wash buffer at RT °. The wash buffer consisted of PBS, 2% heat-inactivated fetal bovine serum (Hyclone, Logan, Utah) and 0.02% sodium azide (Sigma, St. Louis, Mo.). Next, 100 µl of various concentrations of antibody was added to the cells (starting at 30 ug/ml and using a 3-fold titration) diluted in wash buffer containing 0.005 mg/ml of cytocholasin B (Sigma, St. Louis, Mo.). The cells were gently rocked at RT ° for 3 hours. Next, the cells were washed twice and resuspended in 0.5 ml/tube with cold wash buffer and 10,000 events were collected and analyzed using a Becton Dickinson FACSCalibur and CellQuest software (San Jose, Calif.).

Biacore Assay:

The Biosensor biospecific interaction analysis instrument (BIAcore 2000) uses surface plasmon resonance to measure molecular interactions on a CM5 sensor chip. Changes in the refractive indices between two media, glass and carboxymethylated dextran, caused by the interaction of molecules to the dextran side of the sensor chip, is measured and reported as changes in arbitrary reflectance units (RU) as detailed in the manufacturer's application notes.

The carboxymethylated dextran surfaces on a CM5 sensor chip were activated by derivatization with 0.05 M N-hydroxysuccinimide mediated by 0.2 M N-ethyl-N'-(dimethylaminopropyl) carbodiimide for 7 min. Streptavidin (Sigma S-4762) at a concentration of 500 µg/ml, in 10 mM Na acetate, pH 4.5, was injected onto three surfaces (Flow Cell-2, 3 and 4) at a rate of 5 µl/min and covalently immobilized to the flow cell surfaces with approximately 2500 RU's. 35 µl of 10 mM Na acetate buffer was injected over Flow cell-1 during immobilization in place of antigen to make an activated blank surface to measure non-specific binding. Deactivation of unreacted N-hydroxysuccinimide esters on all four Flow cells was performed using 1M ethanolamine hydrochloride, pH 8.5. Following immobilization, the flow cells are cleaned of any unreacted or poorly bound material with 5 regeneration injections of 5 μl of 50 mM NaOH until a stable baseline was achieved.

Biotinylated CD134-muIg (Ancell 513-030), at a concentration of 10 μg/ml at a flow rate of 5 μl/min was manually injected over Flow cells-2, 3 and 4 to achieve 3 surface densities: Fc-2=150 RU, Fc-3=375 RU and Fc-4=580 RU. The different density surfaces were prepared to monitor the possibility of mass transport limited binding during association phase and rebinding during dissociation, both artifacts that are influenced by surface density that must be avoided.

A dilution series of the OX40R antibodies were prepared over a concentration range of 666 nM to 66 pM by half logs in running buffer (0.01M HEPES, pH 7.4, 0.15M NaCl, 3 mM EDTA, 0.005% polysorbate 20 (v/v)). The flow rate was set at 5 μl/min and 25 μl of each concentration point sample was injected over the sensor chip with a regeneration injection of 5 μl of 50 mM NaOH between each concentration of antibody injected. Dissociation time was 5 min. The data was analyzed using BIAevaluation 3.0 global fit software (separate analysis of each concentration point).

Epitope Characterization:

300-19 cells expressing a recombinant human OX40-CD40 fusion construct corresponding to 1-235 amino acid sequence of OX40 (extracellular and transmembrane domain) and 216-278 amino acid sequence of CD40 (intracellular domain) was used for antibody epitope analysis. The OX40-CD40 expressing cell line was grown in RPMI medium (Gibco, Grand Island, N.Y.) supplemented with 10% fetal calf serum (Hyclone, Logan, Utah), 10 mM hepes, 1% penicillin-streptomycin, 2 mM L-glutamine, 0.1 mM non-essential amino acids and 0.05 mM 2-mercaptoethanol (Gibco, Grand Island, N.Y.). 300-19.hCD134.2 cells ($5\times10^5$/tube) were washed once in 3 mls of cold wash buffer (PBS, 2% FBS and 0.02% sodium azide). The cell supernatant was aspirated and 100 μl of wash buffer containing 300 μg/ml of primary unconjugated OX40 reactive antibody was added to the cell pellet, mixed and incubated for 30 minutes at 4° C. Next, a fluorochrome labeled secondary antibody was added to the tube, mixed and incubated for an additional 30 minutes at 4° C. The OX40 reactive fluorochrome labeled antibodies included either 10 μl of phycoerythrin (PE) labeled Ber Act 35 (Caltag Laboratories, Burlingame, Calif.), PE-labeled L106 (BD Pharmingen, San Jose, Calif.) or Alexa Fluor 647 conjugated OX40R antibody. The OX40R antibody was labeled with fluorochrome using the Alex Fluor 647 protein labeling kit as described by the manufacturer (Molecular Probes, Eugene, Oreg.). After staining, cells were then washed 3 times with wash buffer, resuspended in cold wash buffer and 10,000 events were collected and analyzed using a Becton Dickinson FACSCalibur and CellQuest software (San Jose, Calif.). Antibodies were demeaned as binding to the same epitope when the primary antibody blocked the staining of the secondary fluorochrome labeled antibody by more than 80%.

Antibody OX40 Ligand-OX40R Inhibition Assay:

Antibodies were tested for their ability to block the binding of the 300-19 human-OX40 ligand (L) expressing cells to OX40-human IgG1 fusion protein coated plates. The 300-19-OX40L cell line was grown in RPMI medium (Gibco, Grand Island, N.Y.) supplemented with 10% fetal bovine serum (Hyclone, Logan, Utah), 10 mM HEPES, 1% penicillin-streptomycin, 2 mM L-glutamine, 0.1 mM non-essential amino acids, 0.05 mM 2-mercaptoethanol and 0.5 mg/ml Geneticin (Gibco, Grand Island, N.Y.). The OX40-human IgG1 fusion protein contains the first 220 amino acids of the extracellular OX40 protein. The fusion protein was coated onto to Nunc Maxisorb plates (Nunc, Roskilde, Denmark) in 100μ/well (5 μg/ml) in coating buffer (BupH, Carbonate-Bicarbonate buffer, Pierce, Rockford, Ill.) and incubated overnight at 4° C. Next, plates were blotted on a paper towel to remove fluid, blocked with 200 μl/well with blocking buffer (5% Carnation Milk diluted in PBS) and incubated at RT ° for two hours. Plates were washed with PBS and various dilutions of antibody diluted in PBS were then added (50 μl/well) to the assay plate and incubated at RT ° for 30 minutes. Next, 50 μl/well of cells in PBS at $6\times10^5$/well were added to the antibody containing wells and incubated for an additional 60 minutes at 37° C. in a 5% $CO_2$ humidified chamber. The plates were gently washed 2 times with PBS to remove non-adherent cells and cell activity in the wells was measured by adding 200 μl of a 20 ug/ml Fluorescein Diacetate (Sigma, St. Louis, Mo.) PBS solution to each well. The plates were incubated at 37° C. in a 5% $CO_2$ humidified chamber for 90 minutes and read using a spectrophotometer at 490 (Spectra Max 340, Molecular Devices, Sunnyvale, Calif.).

OX40R Antibody Selectivity Assay (ELISA):

Maxisorb 96-well plates (Nunc, Roskilde, Denmark) were coated with 100 μl of human TNFα receptor family member fusion proteins at 0.25 μg/ml diluted in BupH™ Carbonate buffer, pH 9.4 (Pierce, Rockford, Ill.) and incubated overnight at 4° C. The selectivity receptor fusion proteins tested included CD40-Ig (Alexis Biochemicals, San Diego, Calif.), CD137-Ig (R&D Systems, Minneapolis, Minn.) and CD271-Ig (Alexis Biochemicals, San Diego, Calif.). Also included as the positive control with each assay was the OX40-Ig fusion protein (in-house construct, Bioexpress, 97/2117). Plates were then washed three times with wash buffer containing 0.05% Tween 20 (Sigma, St Louis, Mo.) diluted in PBS and blocked with 300 μl of 0.5% BSA (Sigma, St Louis, Mo.) in PBS (Sigma, St Louis, Mo.) for 1 hour at RT °. Next, the plates were washed and 100 μl/well of anti-human OX40 reactive antibodies were added to the plates at various concentrations and incubated for 1 hour at RT °. Plates were thoroughly washed three times and OX40R antibody binding was detected with a horse radish peroxidase labeled anti-human kappa chain antibody (Bethyl Laboratories, Montgomery, Tex.) at 25 ng/ml for 1 hour at RT °. Plates were then washed three times which was followed by the addition of 100 μl/well of 1-Step Turbo-TMB substrate (Pierce, Rockford, Ill.) for 30 minutes at RT °. The reaction was stopped by adding an equal volume of 2M $H_2SO_4$. Absorbance was read at 450 nm on a Molecular Devices Spectra Max 340 (Molecular Devices, Sunnyvale, Calif.).

Species Cross-Reactivity:

Cell Lines Expressing OX40R: The 300-19 cell line expressing either a recombinant human OX40-CD40 fusion construct corresponding to 1-235 of OX40R (extracellular and transmembrane domain) and 216-278 of CD40 (intracellular domain) or the entire cynomolgus OX40R protein.

Preparation of Human T Lymphocytes:

Human whole blood was collected into heparinized syringes (Baxter; Deerfield, Ill.) and then immediately transferred to Sigma Accuspin tubes (Sigma, St. Louis, Mo.) for the isolation of peripheral blood mononuclear cells (PBMC) as described by the manufacturer. The PBMC were washed twice with DPBS and T lymphocytes were isolated using a T cell purification column as described by the manufacturer (R & D Systems, Minneapolis, Minn.). Briefly, PBMCs were resuspended in 2 mls of column buffer and loaded into a pre-washed T cell isolation column. PBMCs were incubated for 10 minutes at room temperature and T cells were eluted with column buffer, washed one time and resuspended TCM at $2\times10^6$/ml consisting of RPMI 1640 (Sigma, St Louis, Mo.) supplemented with 10% fetal bovine serum (Hyclone, Logan, Utah) and L-glutamine (2 mM), Hepes (10 mM), penicillin (100 U/ml), streptomycin (50 ug/ml) (Gibco, Grand Island, N.Y.). A 2 ml volume of T cells containing an anti-human CD28 antibody at 1 ug/ml (clone 37407, R & D Systems, Minneapolis, Minn.) was added to the wells of a 24 well plate pre-coated with an anti-human CD3 antibody clone UCTH1 (R & D Systems, Minneapolis, Minn.) at 5 µg/ml in PBS. T cell cultures were stimulated for 3 days prior to being tested for human OX40 cross-reactivity by flow cytometry.

Preparation of Cynomolgus PBMCs:

Cynomolgus whole blood was obtained using heparinized vacutainer tubes (BD; Franklin Lakes, N.J.) and was diluted 1:4 in PBS. Diluted whole blood was mixed and 15 mls was carefully layered over an equal volume of Histopaque 1077 (Sigma, St Louis, Mo.). The tubes were spun at 1000×g for 45 minutes at RT ° and the mononuclear PBMC interface was harvested, washed once in PBS and resuspended for 2 minutes at RT ° with ACK lysing buffer (Biosource, Rockville, Md.) to remove any RBCs. After a PBS wash, the PBMCs were counted and readjusted to $1\times10^6$/ml in tissue culture medium (TCM). TCM consisted of RPMI 1640 (Sigma, St Louis, Mo.) supplemented with 10% fetal bovine serum (Hyclone, Logan, Utah) and L-glutamine (2 mM), Hepes (10 mM), penicillin (100 U/ml), streptomycin (50 ug/ml) purchased from Gibco (Grand Island, N.Y.). Next, 2 mls of the PBMC preparation containing an anti-human CD28 cross-reactive antibody (clone CD28.2, BD Biosciences, San Diego, Calif.) was added to the wells of a 24 well plate (Costar, Corning, N.Y.) pre-coated with an anti-monkey CD3 antibody (clone FN18, Biosource, Camarillo, Calif.) at 10 µg/ml in PBS. PBMC cultures were stimulated for 4 days prior to being tested for human OX40 cross-reactivity by flow cytometry.

Preparation of Rabbit PBMCs:

Rabbit whole blood was drawn into heparinized vacutainer tubes (BD; Franklin Lakes, N.J.) and immediately diluted 1:3 with warm HBSS (Gibco, Grand Island, N.Y.). After mixing, 5 mls of the diluted blood was carefully layered over and equal volume of Lympholyte-Rabbit (Cedarlane Laboratories, Westbury, N.Y.) and centrifuged for 30 minutes at 25° C. The PBMC interface was collected, washed twice with PBS and resuspended to $2\times10^6$/ml in TCM containing PHA at 10 ng/ml (Remel, Lenexa, Kans.). The cells were cultured for 24-48 hours.

Preparation of Canine PBMCs:

Canine whole blood was collected using heparinized vacutainer tubes (BD; Franklin Lakes, N.J.). Next, the blood was mixed with an equal volume of warm HBSS (Gibco, Grand Island, N.Y.). Four mls of diluted blood was slowly layered over 3 mls of Lympholyte-M (Cedarlane Laboratories, Westbury, N.Y.) in a 15 ml conical tubes. The tubes were centrifuged for 20 minutes at 800×g and the PBMC interface was collected, washed twice with HBSS and resuspended in TCM at $2\times10^6$/ml. PBMCs were added to the wells of a 24 well plate (2 ml/well) and the cells were stimulated with 2 µg/ml of ConA (Sigma, St. Louis, Mo.) for 48 hours.

Preparation of Murine and Rat PBMCs:

Rat whole blood collected in heparinized syringes was diluted 1:3 in warm HBSS. Next, 5 mls was carefully layered over an equal volume of Lympholyte-Rat (Cedarlane Laboratories, Westbury, N.Y.). The tubes were centrifuged for 20 minutes at 1500 RPM. The PBMCs interface was collected, washed twice and the cell pellet was re-adjusted to $2\times10^6$/ml in TCM. Two mls of cells were added to each well of a 24 well plate and stimulated for 24-48 hours with PHA (Remel, Lenexa, Kans.) at 10 ng/ml prior to flow cytometry staining.

Flow Cytometry Staining for Species Cross-reactivity:

Stimulated mouse, rat, rabbit, dog and cynomolgus PBMCs and the 300-19 cell line expressing the cynomolgus OX40 receptor were used to test for human OX40 antibody species cross-reactivity. Human OX40 expressing activated T lymphocytes and OX40 transduced 300-19 cells were used as positive controls. Cells ($5.0\times10^5$/tube) were washed once in cold wash buffer (PBS, 2% FBS and 0.02% sodium azide) and 100 µl/tube of Alexa Fluor 647 conjugated control or OX40 reactive antibodies at 5 ug/ml was added to each tube. The antibodies were labeled using an Alex Fluor 647 protein labeling kit as described by the manufacturer (Molecular Probes, Eugene, Oreg.). The cells were incubated in the dark with fluorochrome antibodies on ice for 30 minutes, washed three times and resuspended in 0.5 ml wash buffer for analysis. Antibody staining was measured and analyzed using a Becton Dickinson FACSCalibur and CellQuest software (San Jose, Calif.).

Luciferase Activity Assay:

293T cells containing the extracellular domain of OX40 and the intracellular domain of CD40 fused to a NfkB reporter containing luciferase were prepared. Cells were harvested, washed and resuspended into phenol red free complete medium (DMEM containing 10% fetal bovine serum, HEPES buffer, nonessential amino acids and L-glutamine) at density of $0.5\times10^6$ cell/ml. 80 ul of cells were plated into each assay well of a 96 well plate (PerkinElmer, parts number 6005680). Test antibodies were added to each well alone or in the presence of a cross linking antibody Fab' goat anti-human IgG (Jackson ImmunoResearch, West Grove, Pa.). The plate was incubated overnight at 37 C. 100 ul of luciferase (Promega, Bright-glo luciferassay system, Cat. #E2620) was added the next day and the amount of luciferase activity was measured using a syntillation counter (TopCount, Packard-NXT).

Human αCD3 IL-2 Assay:

Human whole blood was collected in heparinized (Baxter; Deerfield, Ill.) syringes, layered over Accuspin tubes (Sigma; St. Louis, Mo.) and centrifuged for 15 minutes at 2000 rpm's. The buffy coat was collected, washed with PBS (Sigma, St. Louis, Mo.), and red blood cells lysed with water. T cells were separated out by human $CD3^+$ enrichment columns (R&D; Minneapolis, Minn.), counted and adjusted to $1\times10^6$/ml in RPMI media (Gibco; Grand Island, N.Y.) containing: 10% fetal calf serum (Hyclone; Logan, Utah), 10 mM hepes, 1% penicillin-streptomycin, 2 mM L-glutamine and 0.1 mM non-essential amino acids (all Gibco). Concurrently, human anti-CD3ε clone #UCHT1 (R&D systems, Minneapolis, Minn.) was placed at 2.5 µgs/ml in PBS into 24 well plates (Costar; Corning, N.Y.) and incubated for 2 hours at 37° C. The plates were washed 3× with PBS and the following added to the wells: T cells at $1\times10^6$/well, serial dilutions of OX40 antibodies (or $IgG_2$ KLH control) and $F(ab')_2$ goat anti-human IgG Fcγ to cross link (added at 2.5 ug/mL). Supernatants were pulled at 48 and 72 hours and IL-2 levels were assessed by ELISA (R&D).

Cynomolgus αCD3 IL-2 Assay:

Cynomolgus monkey whole blood was collected in heparinized tubes (BD; Franklin Lakes, N.J.), diluted 1:4 in PBS, layered over Histopaque 1077 (Sigma, St Louis, Mo.) and centrifuged for 45 minutes at 2200 rpm's. The buffy coat was collected, washed with PBS, and red blood cells lysed with water. Cells were adjusted to 1×10$^6$/ml and added to 24 well plates that had been pre-coated for 2 hours with varying concentrations of monkey anti-CD3, clone FN-18 (Biosource; Camarillo, Calif.) at 37° C. Serial dilutions of OX40 antibody (or IgG$_2$ KLH control), as well as F(ab')$_2$ goat anti-human IgG Fcγ at 2.5 ug/mL were added to the wells. Supernatants were collected at 24 and 48 hours and IL-2 levels were assessed by ELISA (Biosource, Camarillo, Calif.).

Alloantigen Primed T Cells Assay:

Freshly isolated human T cells (see above) were incubated with mitomycin c treated allogeneic tumor cells (Raji) for 3-4 days. T cells were then harvested, washed, and rested for 1 day in fresh media prior to stimulating with 11D4. The level of IL-2 was assessed 24 hours latter by ELISA (R&D systems, Minneapolis, Minn.).

B. In Vivo Study Procedures

SCID-Beige Human Tumor Models Using Mice Engrafted with Human T cells and Dendritic Cells:

SCID-beige mice (Taconic #CBSBG-MM) were acclimated for 5-7 days after arrival prior to use. The following tumor cell lines were used: RAJI, ATCC #CCL-86; BT-474, ATCC #HTB-20; PC-3, ATCC#-1435; and LoVo, ATCC #CCL-229.

Purified T lymphocytes (T cells) and monocyte derived dendritic cells were prepared from human blood as follows: Human mononuclear cells were collected from heparinized blood using Sigma Accuspin Tubes #A7054. Cells were collected, placed in a T75 flask, and incubated for 3 hrs at 37° C. in a humidified incubator under 5% CO$_2$. The non-adherent cells were collected and saved (see below). The flask containing the adherent cells was incubated with 20 ml RPMI complete medium (containing 10% fetal calf serum) supplemented with IL-4 (R&D) at 10 ng/ml and GM-CSF (R&D) at 100 ng/ml. The culture was then incubated for 6-7 days at 37° C. in a humidified incubator under 5% CO$_2$. The non-adherent monocyte derived dendritic cells were then collected by decanting and rinsing flask several times with RPMI complete medium.

The initial non-adherent mononuclear cells were used to purify T cells via high affinity negative selection using T cell enrichment columns (R&D) as per manufacturer's instructions. Purified T cells were cryo-preserved in Recovery-Cell Culture Medium at 10$^7$/ml and stored in liquid Nitrogen until use. Tumor cells (1×10$^7$) were injected subcutaneously (SC) with T cells (1×10$^6$) and monocyte-derived dendritic cells (5×10$^5$) from the same donor, at 0.2 mL/mouse. Tumor growth was monitored over time with calipers.

C. Results for Antibody 11D4

(1) In Vitro Studies:

Certain properties of antibody 11D4 from in vitro studies are summarized in Table 3.

Antibody 11D4 Binds to the OX40R with High Affinity.

This was demonstrated by using an IgG1 fusion protein containing the extracellular domain of the OX40R and on whole cells (OX40R+ transfected cells and activated primary T cells). In examples using the IgG1 fusion protein, 11D4 bound to the extracellular domain of the OX40R with an EC$_{50}$ of 0.5+/−0.18 µg/mL (3.5 nM). This binding was confirmed on 300-19 pre-B cells expressing the full length extracellular domain of the OX40R (no binding was observed on parental 300-19 cells). The EC$_{50}$ for binding to OX40R transfected cells was 0.2+/−0.16 µg/mL (1.7 nM). In order to confirm that binding was observed on primary T cells, peripheral blood T cells were isolated from multiple human donors and stimulated with anti-CD3 and anti-CD28 for 2 days to upregulate the expression of the OX40R. Saturation binding data on these T cells indicated that 11D4 binds with an EC$_{50}$ of 0.6+/−1.0 µg/mL (4.0 nM, N=17 donors). These data demonstrate that 11D4 avidly binds to the OX40R.

In order to further characterize this binding, data was collected to assess the region on the extracellular domain of the OX40R where 11D4 interacts and to also determine whether the receptor was internalized following binding. Competition binding data to the OX40R IgG1 fusion protein indicated that 11D4 competes for binding with OX40 ligand expressing cells providing evidence that 11D4 interacts at the ligand binding region of the receptor. In addition, 11D4 does not cross-compete with two commercially available OX40R antibodies, BerAct35 and L106, for binding to T cells as assessed by FACS analysis. FACS analysis using non-competing detection antibodies indicated that the OX40R was not internalized following the pre-incubation of primary, activated T cells with 11D4 for 30 minutes. Its binding affinity, determined by Biacore analysis using the OX40R extracellular domain fusion protein as the immobilized ligand, indicated that the equilibrium dissociation constant (KD) of 11D4 for binding was 0.48 nM. These analyses also estimated the off rate constant (kd) of 11D4 to be 5.72 E-05 l/s. Therefore, 11D4 binds with high affinity to the ligand binding region of the OX40R, has a slow off-rate constant, and does not internalize the receptor following binding.

Antibody 11D4 Selectively Binds to the OX40R.

Figure 1B:
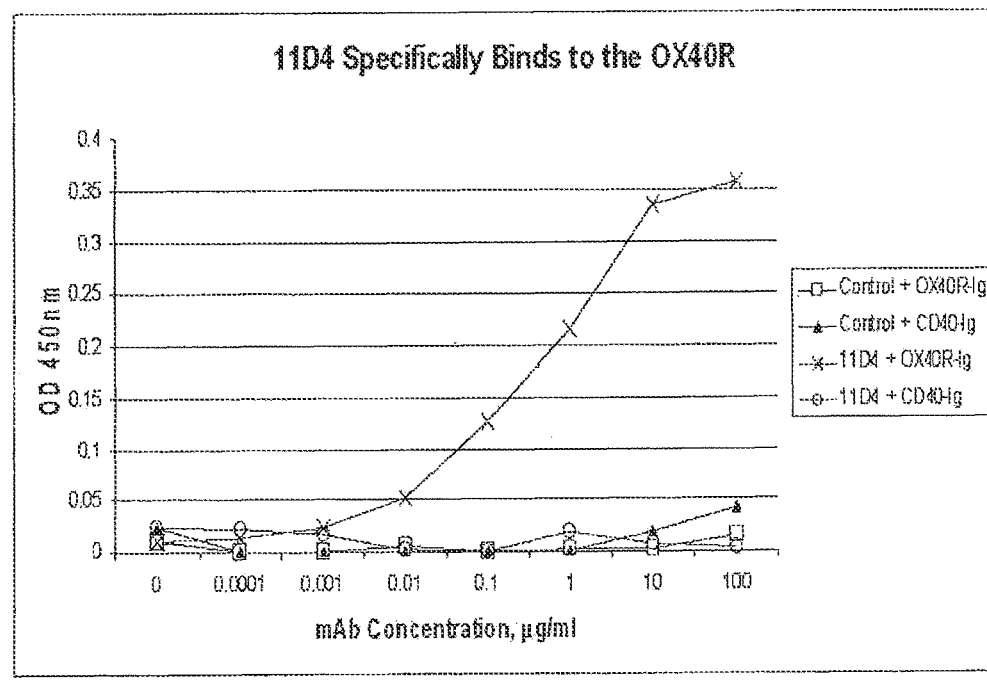

The selectivity of 11D4 for the OX40R was assessed against other members of the TNFR superfamily using data related to IgG1 fusion protein constructs containing the respective extracellular domain of the related receptor. These receptors included the CD40 receptor, 4-1BB receptor (CD137) and the nerve growth factor receptor (CD271). In all cases, no significant binding was observed at concentrations up to 100 µg/mL (700 nM) on these receptors. When compared to binding observed to the OX40R fusion protein (EC$_{50}$=0.5 ug/ml), these data demonstrate that 11D4 is >100-fold selective for the OX40R vs other related family members tested. (See FIGS. 1a and 1b).

Functional Activity of Antibody 11D4:

The functional activity of 11D4 was demonstrated on both OX40R+ transfected cells and on primary T cells. In these assays, 11D4 demonstrated agonist activity when added to cells with or without a secondary antibody, F(ab')$_2$ goat anti-human IgG Fcγ.

Figure 2:
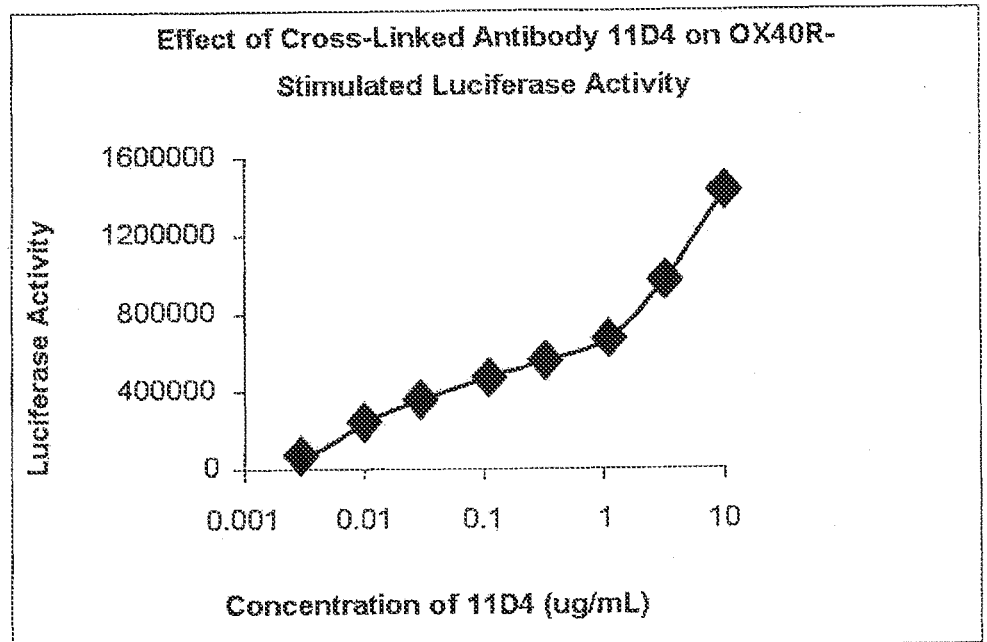
FIG. 2 is a graph showing the effect of cross-linked antibody 11D4 on OX40R-stimulated luciferase activity.

In the first set of experiments, 11D4 was assessed for agonist activity using 293 cells transfected with the extracellular and transmembrane domain of the OX40R fused to the intracellular domain of CD40 with an NFkB luciferase reporter. In this assay, 11D4 enhanced signaling through the OX40R with a mean EC$_{50}$ of 0.33 µg/mL (2.2 nM, N=4). A representative concentration-response curve for the induction of luciferase by 11D4 is shown in FIG. 2. In the absence of the F(ab')$_2$ secondary antibody, the magnitude of luciferase activity was reduced 4-fold along with the EC$_{50}$.

Figure 3:
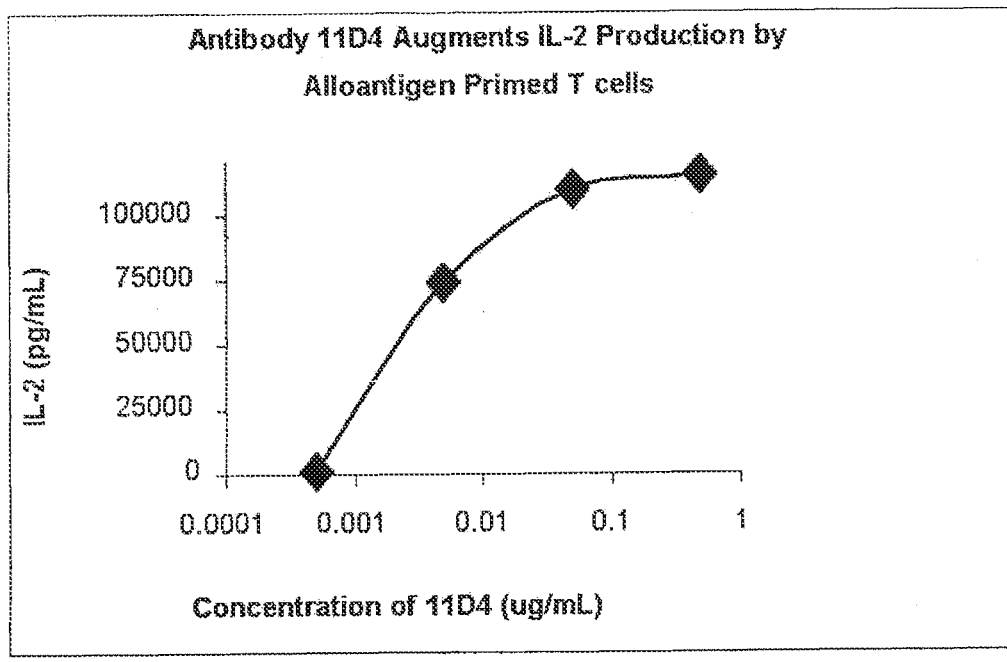
FIG. 3 is a graph showing the effect of antibody 11D4 on IL-2 production by alloantigen primed T cells.

As further evidence for the agonist activity of 11D4, antigen-specific T cells were generated. Freshly isolated human T cells were incubated with mitomycin c treated allogeneic tumor cells (Raji) for 3-4 days. T cells were then harvested, washed, and rested for 1 day in fresh media prior to stimulating with 11D4. FACS analysis indicated a high level of OX40R expression on these cells even after resting. 11D4 induced high levels of IL-2 by these cells, in some cases exceeding 100 ng/mL (FIG. 3). The average EC$_{50}$ for this response from 2 separate examples was 0.008+/−0.006 μg/mL. In the absence of 11D4, only minimal levels of IL-2 were secreted by these cells.

Figure 4:
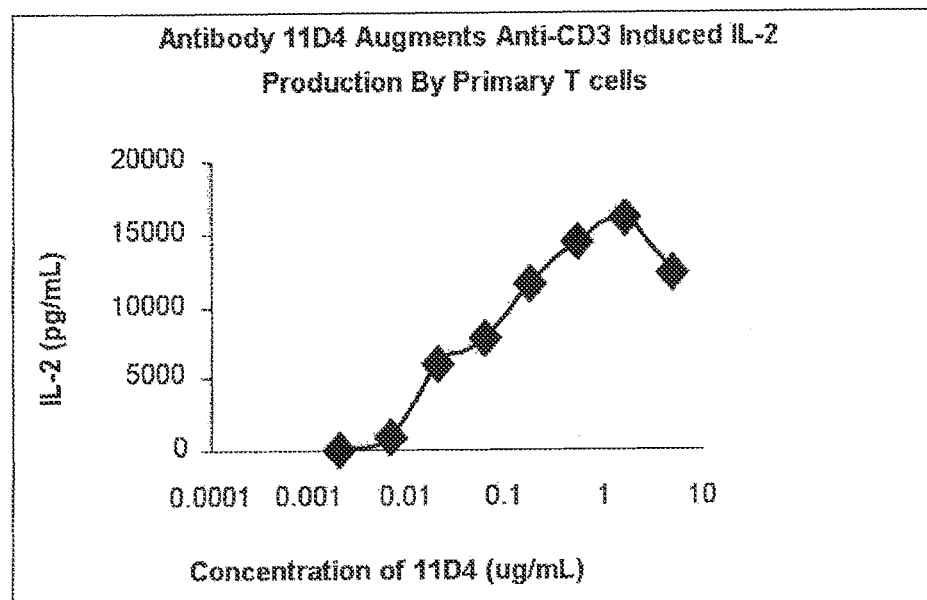
FIG. 4 is a graph showing the effect of antibody 11D4 on anti-CD3 induced IL-2 production by primary T cells.

11D4 also enhances the IL-2 production by the primary human T cells stimulated by anti-CD3. Although the signal to noise ratio in this assay was low in some assays due to the induction of IL-2 by anti-CD3 alone, 11D4 enhanced IL-2 production when added with F(ab')$_2$ goat anti-human IgG Fcγ. No activity was observed for 11D4 on freshly isolated T cells in the absence of anti-CD3. The magnitude of IL-2 augmentation by 11D4 ranged from 2.3 to 57-fold vs. anti-CD3 alone depending on the donor and the amount of IL-2 generated by anti-CD3. The effect of 11D4 on IL-2 production by primary human T cells stimulated with 2.5 μg/mL anti-CD3 is represented in FIG. 4 (using an 8 point concentration curve with 1:3 dilutions). The average $EC_{50}$ calculated from those data which used 8-point concentration response curves was 0.042+/−0.01 μg/mL (see Table 4).

Figure 5:
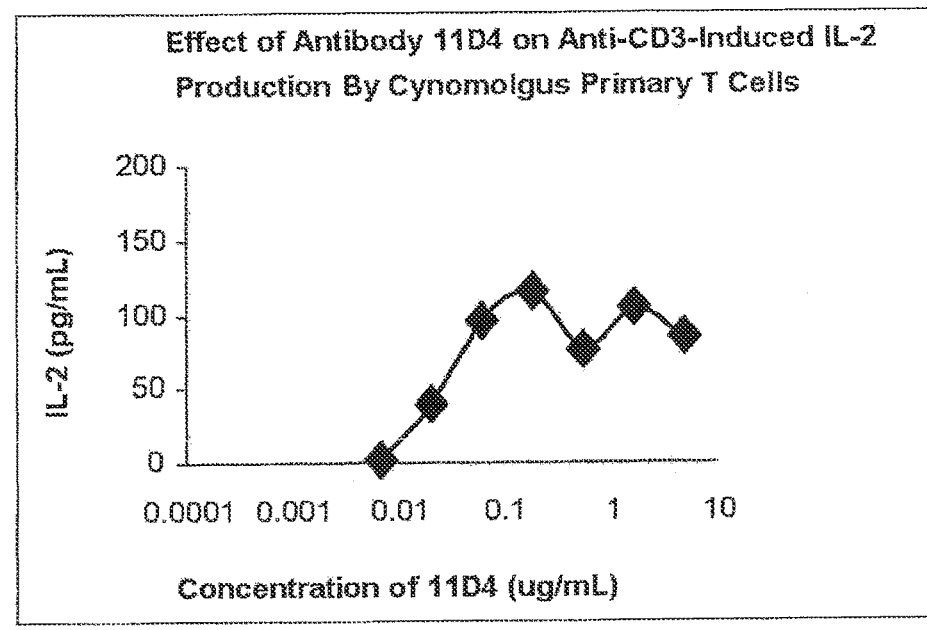
FIG. 5 is a graph showing the effect of antibody 11D4 on anti-CD3 induced IL-2 production by cynomolgus primary T cells.

Functional activity of 11D4 on IL-2 production was also assayed using monkey cells stimulated with anti-CD3 and 11D4 (along with F(ab')$_2$ secondary antibody). Results are represented in FIG. 5 and Table 5. These data indicated that the $EC_{50}$ for 11D4 was similar between monkey and human cells (0.022 vs 0.042 μg/mL for human cells), but the magnitude of IL-2 induced above that of anti-CD3 alone was significantly less using Cynomolgus T cells (approx. 35-fold, 5762+/−4748 pg/mL IL-2 for human cells (N=21) vs 261+/−294 pg/mL IL-2 for monkey cells (N=9).

Figure 6:
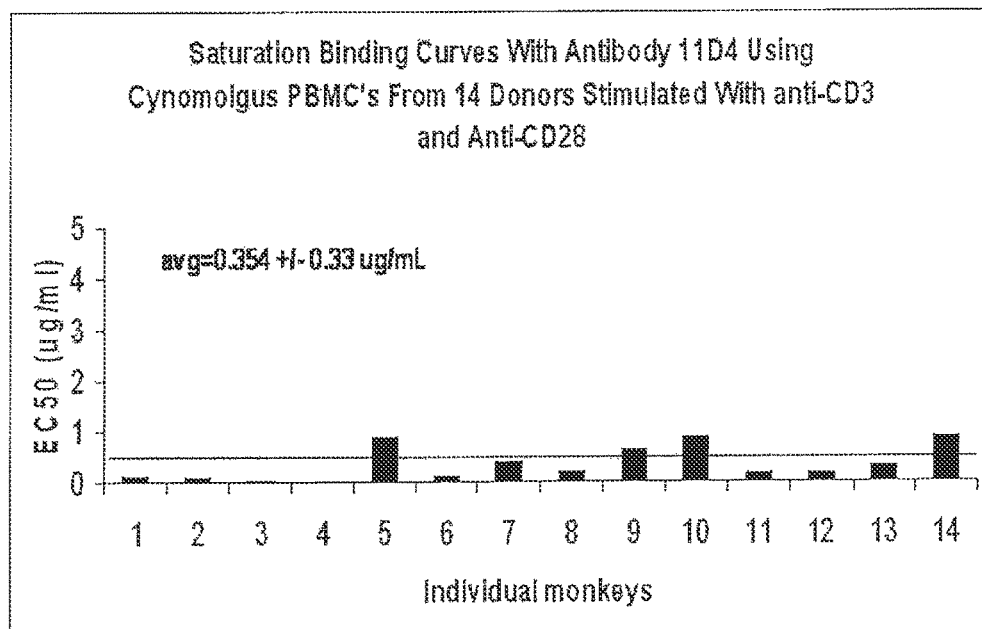
FIG. 6 shows the saturation binding curves with antibody 11D4 using cynomolgus PBMC's from 14 donors stimulated with anti-CD3 and anti-CD28.
Figure 7:
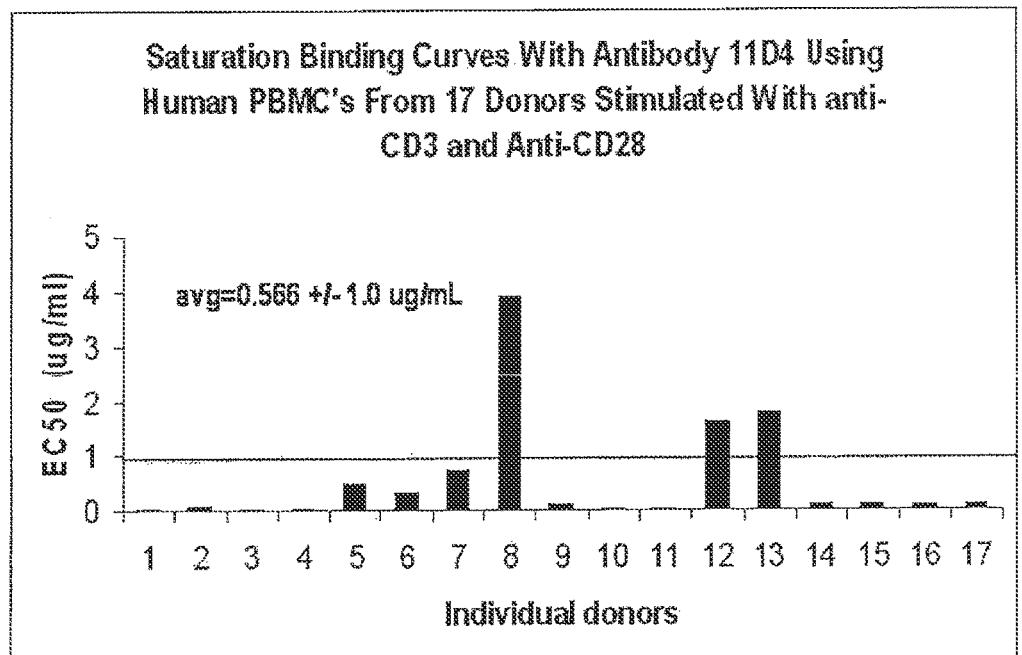
FIG. 7 shows the saturation binding curves with antibody 11D4 using human PBMC's from 17 donors stimulated with anti-CD3 and anti-CD28.

Species Cross-Reactivity:

11D4 was assessed for its ability to bind to T cells from multiple species. T cells were isolated from mouse, rat, rabbit, dog, and monkey and activated with either anti-CD3 plus anti-CD28 or mitogen. No binding was observed to mouse, rat, rabbit or dog cells as indicated by FACS analysis. The lack of binding to mouse OX40R was also confirmed by ELISA using a commercially available fusion protein containing the extracellular domain of the murine OX40R. In contrast, 11D4 binds to Cynomolgus monkey T cells as determined in a saturation binding assay by FACS. The range of $EC_{50}$ values obtained using different monkeys is shown in FIG. 6. For comparison, the range of $EC_{50}$ values obtained using human cells is shown in FIG. 7. Although variable, the range of $EC_{50}$ values was similar between monkey and human cells (mean values are 0.354 μg/mL for monkey vs 0.566 μg/mL for human cells).

(2) In Vivo Studies:

The lack of 11D4 cross-reactivity with the murine OX40R required the development of a xenogenic tumor model using Severe Combined Immunodeficient (SCID) beige mice. SCID-beige mice lack murine T and B lymphocytes and NK cells making them ideal recipients for the engraftment of human immune cells and the growth of human tumors. Four tumor cell lines representing diverse tumor types were tested in this in vivo model. None of the tumor lines expressed OX40R. In all cases, tumor cells ($1 \times 10^7$) were injected subcutaneously (SC) with T cells ($1 \times 10^6$) and monocyte derived dendritic cells ($5 \times 10^5$) from the same donor. 11D4 administered by intraperitoneal (IP) injection inhibited tumor growth up to 98% in these models as summarized in Table 6. The IP route of administration was chosen for 11D4 due to its ease of administration and rapid dissemination into the peripheral blood.

Figure 8:
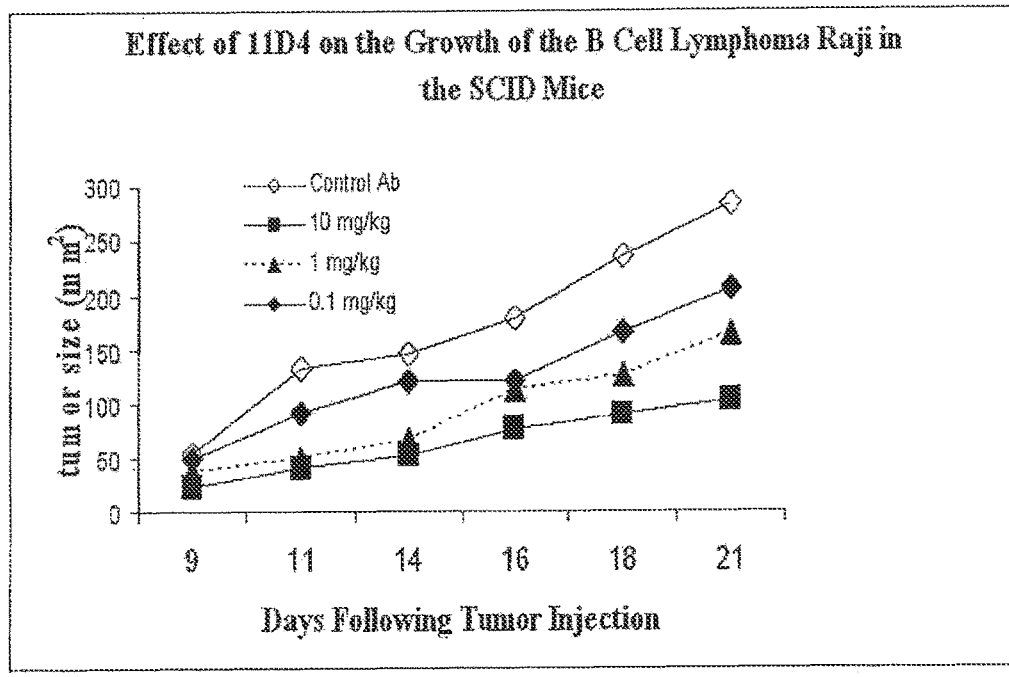
FIG. 8 is a graph showing the effect of antibody 11D4 on the growth of B cell lymphoma Raji in SCID mice.
Figure 9:
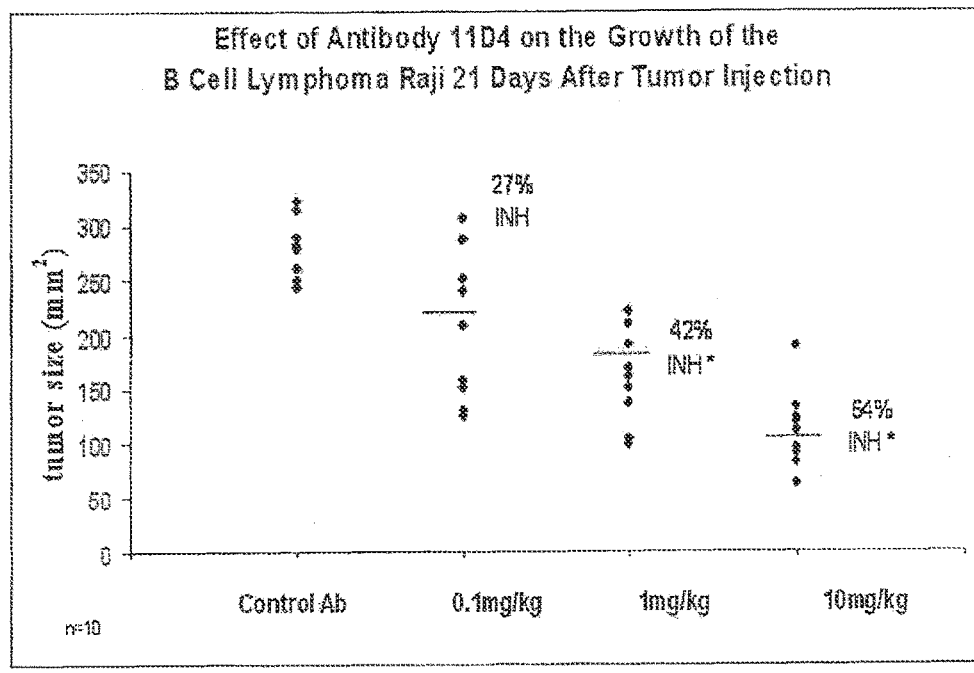
FIG. 9 is a graph showing the effect of antibody 11D4 on the growth of B cell lymphoma Raji 21 days after tumor injection.

Efficacy of 11D4 Against a B Cell Lymphoma in SCID-Beige Mice:

SCID-beige mice were injected SC with the Burkitt's B cell lymphoma, Raji, together with human T cells and monocyte-derived dendritic cells. Mice received a single IP injection of either 11D4 or an isotype control antibody (IgG2 anti-KLH) at the time of tumor injection. As shown in FIG. 8, 11D4 decreased the rate of tumor growth in treated animals. The tumor size in each individual animal (N=10) on day 21 after challenge is shown in FIG. 9, illustrating 64% inhibition in tumor growth by a dose level of 10 mg/kg. No activity was observed in the absence of T cells and dendritic cells.

Figure 10:
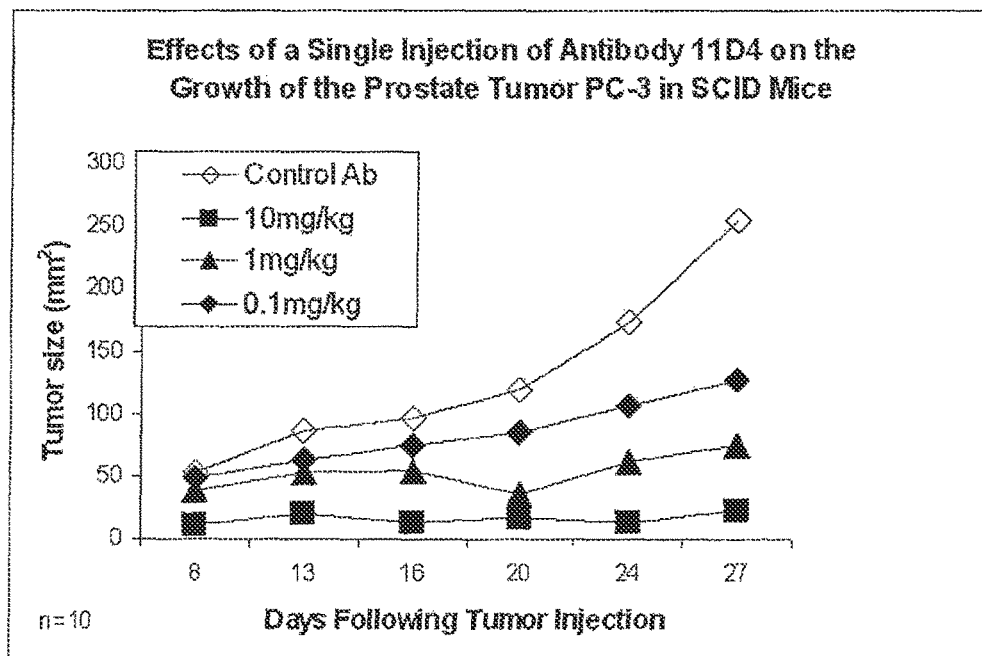
FIG. 10 is a graph showing the effects of a single injection of antibody 11D4 on the growth of the prostate tumor PC-3 in SCID mice.
Figure 11:
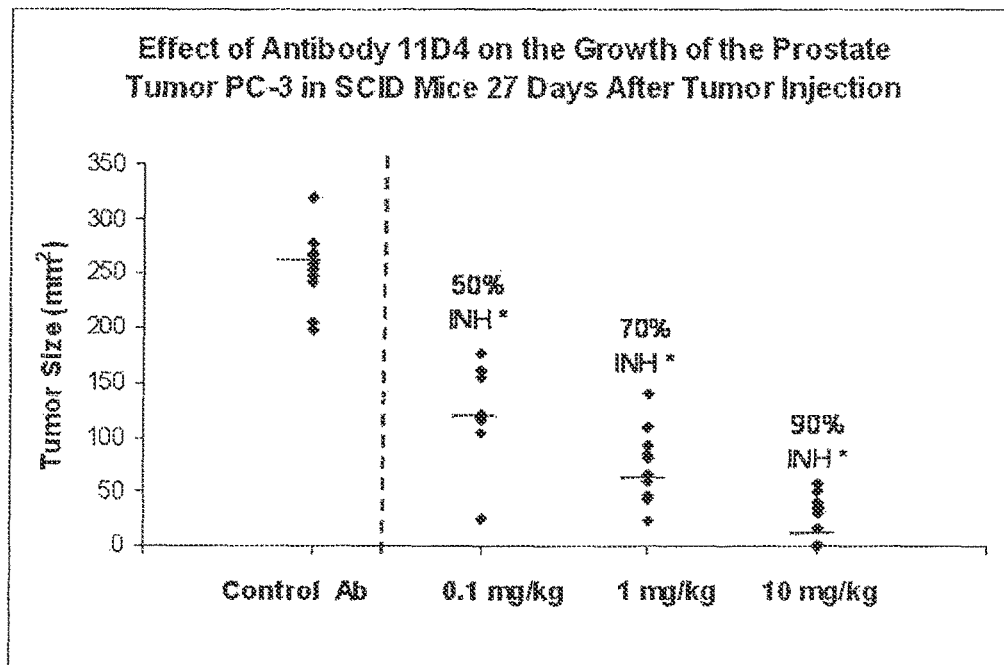
FIG. 11 is a graph showing the effect of antibody 11D4 on the growth of the prostate tumor PC-3 in SCID mice 27 days after tumor injection.

Efficacy of 11D4 in a Prostate Tumor Model:

SCID-beige mice were injected SC with the prostate adenocarcinoma PC-3 together with human T cells and monocyte-derived dendritic cells. Mice received a single IP injection of either 11D4 or an isotype control antibody (IgG2 anti-KLH) at the time of tumor injection. The results, which are represented in FIG. 10, show that 11D4 treatment resulted in a dose-dependent inhibition of tumor growth. The tumor size in each individual animal (N=10) from this study on day 27 after challenge is shown in FIG. 11, illustrating a 70% inhibition in tumor growth when animals were administered a single injection of 1.0 mg/kg 11D4, and 90% inhibition at a dose of 10 mg/kg. The plasma levels of 11D4 determined on day 27 in these animals were 6.2 μg/mL at the 1.0 mg/kg dose level.

Figure 12:
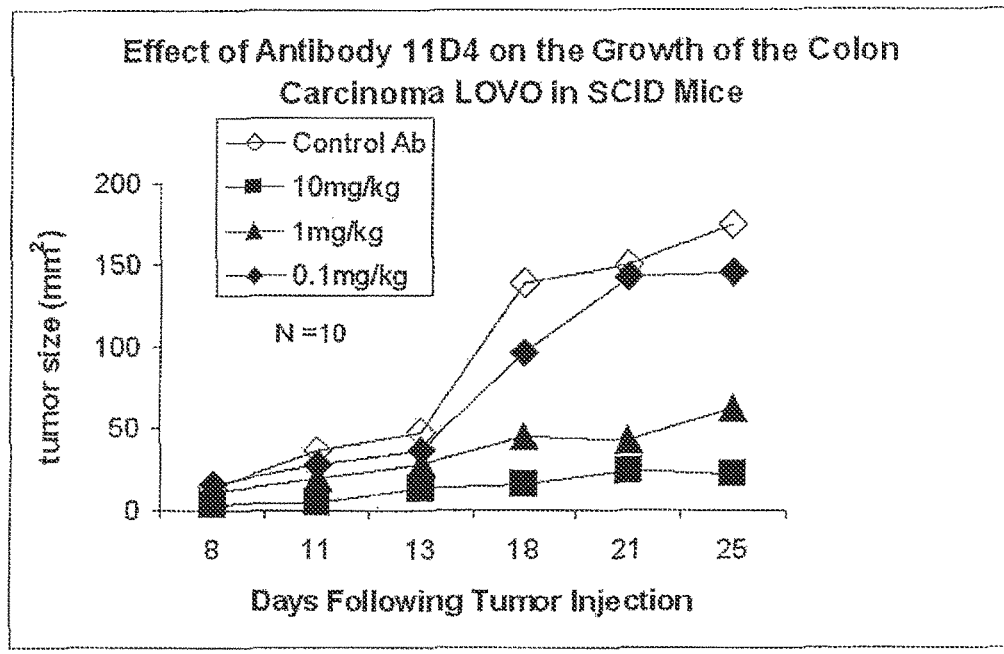
FIG. 12 is a graph showing the effect of antibody 11D4 on the growth of the colon carcinoma LOVO in SCID mice.
Figure 13:
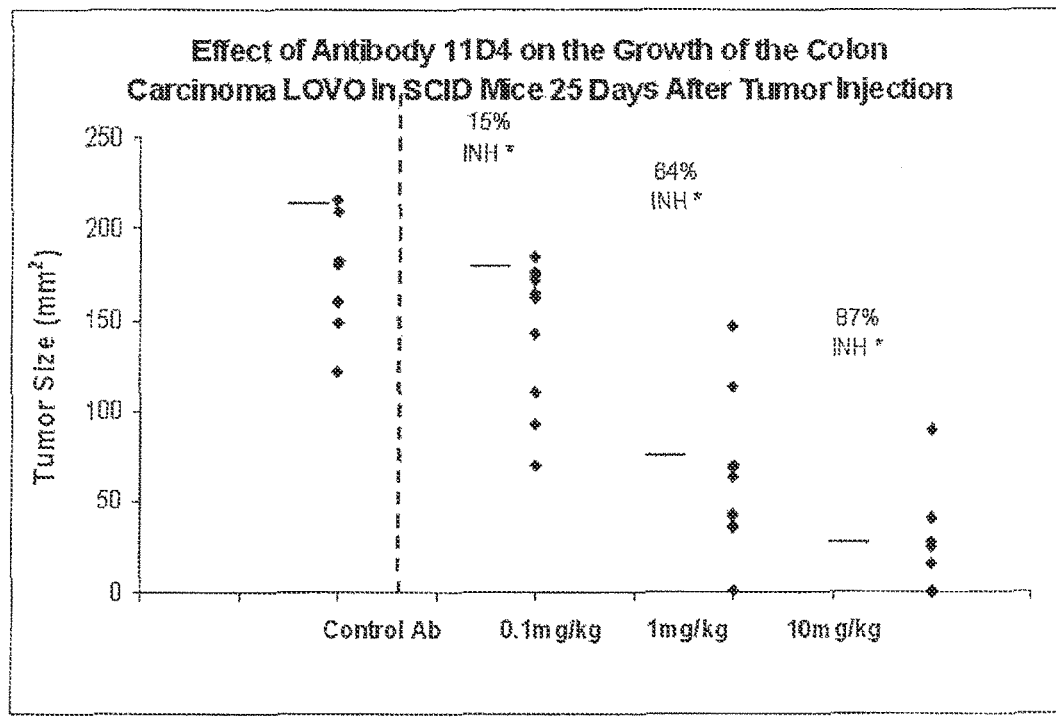
FIG. 13 is a graph showing the effect of antibody 11D4 on the growth of the colon carcinoma LOVO in SCID mice 25 days after tumor injection.

Efficacy of 11D4 in a Colon Carcinoma Tumor Model:

SCID-beige mice were injected SC with the colorectal adenocarcinoma LoVo together with human T lymphocytes and autologous monocyte-derived dendritic cells. Mice received a single IP injection of either 11D4 or a control antibody (IgG2 anti-KLH) at the time of tumor injection. The results, which are represented in FIG. 12, show that 11D4 dose dependency decreased tumor growth in these animals. The tumor size in each individual animal (N=10) from this study on day 27 after challenge is shown in FIG. 13, illustrating a 64% inhibition in tumor growth using a single dose of 1.0 mg/kg and a 87% inhibition of tumor growth at a dose level of 10.0 mg/kg.

Efficacy of 11D4 in a Mammary Carcinoma Tumor Model

Figure 14:
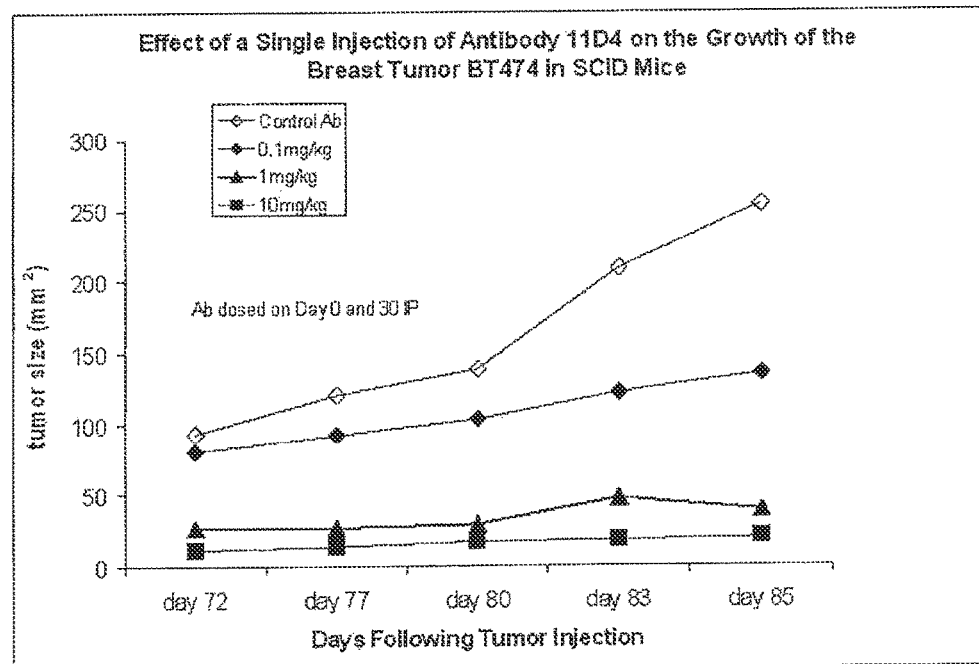
FIG. 14 is a graph showing the effect of antibody 11D4 on the growth of the breast tumor BT474 in SCID mice.
Figure 15:
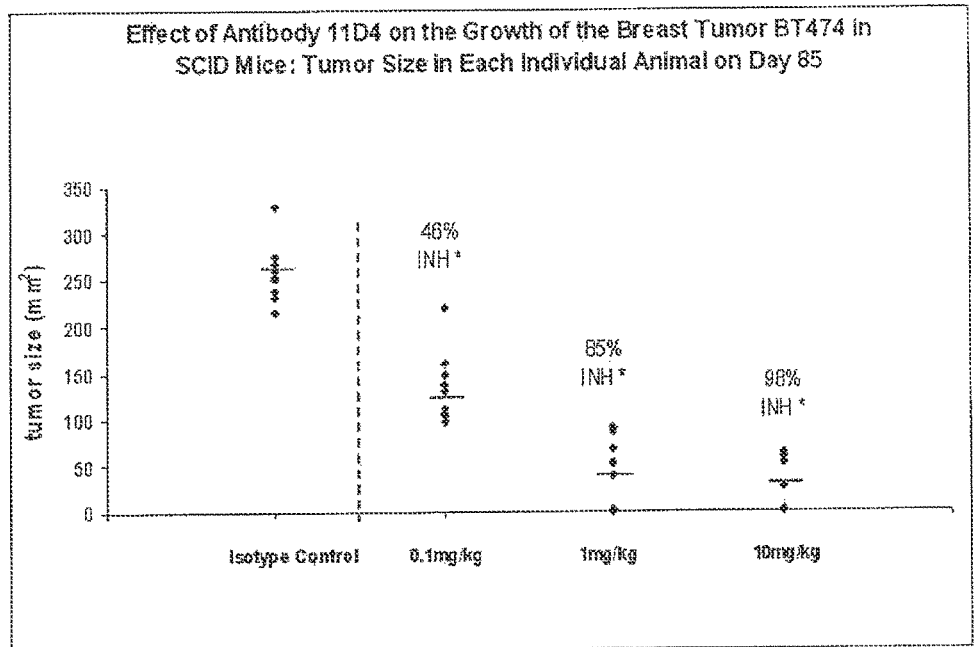
FIG. 15 is a graph showing the effect of antibody 11D4 on the growth of the breast tumor BT474 in SCID mice.

SCID-beige mice were injected SC with the mammary carcinoma BT474 together with human T lymphocytes and autologous monocyte-derived dendritic cells. Mice received two injections (IP) of either 11D4 or a control antibody (IgG2 anti-KLH) at the time of tumor injection and again 30 days later. The results, which are represented in FIG. 14, show that 11D4 decreased tumor growth in these animals. The tumor size in each individual animal (N=10) from this study on day 85 after challenge is shown in FIG. 15 illustrating a 98% inhibition in tumor growth at a dose level of 10.0 mg/kg and 85% inhibition at a dose of 1 mg/kg.

D. Results for Antibody 18D8

(1) In Vitro Studies:

Results from in vitro studies for antibody 18D8 are summarized in Table 7.

Effect of antibody 18D8 on anti-CD3 induced IL-2 production by primary human T cells from different donors are also shown in Table 8.

(2) In Vivo Studies:

Efficacy of 18D8 Against B Cell Lymphoma in a SCID-Beige Mice Model

SCID-beige mice were injected SC with the Burkitt's B cell lymphoma, Raji, together with human T lymphocytes and autologous monocyte-derived dendritic cells. Mice received a single IP injection of either 18D8 or an isotype control antibody (IgG2 anti-KLH) at the time of tumor injection. Ten animals per group were used in each study. The results from two studies are presented in Table 9. The results show that 18D8 produced significant anti-tumor efficacy at the doses of 1.0 mg/kg and 10 mg/kg. No activity was observed in the absence of T cells and dendritic cells, suggesting that this anti-tumor effect may be immune mediated.

Efficacy of 18D8 Against Prostate Tumor in a SCID-Beige Mice Model

SCID-beige mice were injected SC with the prostate adenocarcinoma PC-3 together with human T cells and autologous monocyte-derived dendritic cells. Mice received a single IP injection of either 18D8 or an isotype control antibody (IgG2 anti-KLH) at the time of tumor injection. Ten animals per group were used in the study. The results are presented in Table 9. The results show that 18D8 treatment resulted in a 42%, 90%, and 88% inhibition of tumor growth at the doses of 0.1 mg/kg, 1.0 mg/kg, and 10 mg/kg, respectively.

DEPOSIT INFORMATION

Applicants have deposited a culture of *E. coli* DHα5 containing plasmid that encodes the heavy chain of antibody 11D4 and a culture of *E. coli* DHα5 containing plasmid that encodes the light chain of antibody 11D4 in the American Type Culture collections (ATCC), 10801 University Boulevard, Manassas, Va. 20110-2209, on Jul. 10, 2007, which have been assigned deposit numbers PTA-8524 and PTA-8525, respectively. These deposits were made under the provisions of the Budapest Treaty on the International Recognition of the Deposit of Microorganisms for the Purpose of Patent Procedure and the Regulations thereunder (Budapest Treaty). These deposits will be maintained without restriction in the ATCC depository for a period of 30 years, or 5 years after the most recent request, or for the effective life of the patent, whichever is longer, and will be replaced if the deposits become non-viable during that period. Availability of the deposited materials is not to be construed as a license to practice the invention in contravention of the rights granted under the authority of any government in accordance with its patent laws.

All references cited in this specification, including, without limitation, all papers, publications, patents, patent applications, books, journal articles, are hereby incorporated by reference into this specification in their entireties. The discussion of the references herein is intended to merely summarize the assertions made by their authors and no admission is made that any reference constitutes prior art.

Although the foregoing invention has been described in some detail by way of illustrations and examples for purposes of clarity of understanding, it will be readily apparent to those of ordinary skill in the art in light of the teachings herein that certain changes and modifications may be made to the invention without departing from the spirit or scope of the appendant claims.

TABLE 1

Sequence Identifiers for Antibodies 11D4 and 18D8

| SEQ ID NO: | Antibody | Sequence |
|---|---|---|
| 1 | 11D4 | $V_H$ CDR1 Amino Acid |
| 2 | 11D4 | $V_H$ CDR2 Amino Acid |
| 3 | 11D4 | $V_H$ CDR3 Amino Acid |
| 4 | 11D4 | $V_L$ CDR1 Amino Acid |
| 5 | 11D4 | $V_L$ CDR2 Amino Acid |
| 6 | 11D4 | $V_L$ CDR3 Amino Acid |
| 7 | 11D4 | $V_H$ Amino Acid |
| 8 | 11D4 | $V_L$ Amino Acid |
| 9 | 11D4 | Heavy Chain Amino Acid |
| 10 | 11D4 | Light Chain Amino Acid |

TABLE 1-continued

Sequence Identifiers for Antibodies 11D4 and 18D8

| SEQ ID NO: | Antibody | Sequence |
|---|---|---|
| 11 | 11D4 | $V_H$ Nucleic Acid |
| 12 | 11D4 | $V_L$ Nucleic Acid |
| 13 | 18D8 | $V_H$ CDR1 Amino Acid |
| 14 | 18D8 | $V_H$ CDR2 Amino Acid |
| 15 | 18D8 | $V_H$ CDR3 Amino Acid |
| 16 | 18D8 | $V_L$ CDR1 Amino Acid |
| 17 | 18D8 | $V_L$ CDR2 Amino Acid |
| 18 | 18D8 | $V_L$ CDR3 Amino Acid |
| 19 | 18D8 | $V_H$ Amino Acid |
| 20 | 18D8 | $V_L$ Amino Acid |
| 21 | 18D8 | Heavy Chain Amino Acid |
| 22 | 18D8 | Light Chain Amino Acid |
| 23 | 18D8 | $V_H$ Nucleic Acid |
| 24 | 18D8 | $V_L$ Nucleic Acid |

TABLE 2A

Amino Acid Sequences for Antibody 11D4

| DESCRIPTION | SEQUENCE (Variable region in upper case, constant region in lower case, CDRs underlined) |
|---|---|
| Heavy Chian | EVQLVESGGGLVQPGGSLRLSCAASGFTFS<u>SY SMN</u>WVRQAPGKGLEWVS<u>YISSSSSTIDYADSV KG</u>RFTISRDNAKNSLYLQMNSLRDEDTAVYYC AR<u>ESGWYLFDY</u>WGQGTLVTVSSastkgpsvfp lapcsrstsestaalgclvkdyfpepvtvswn sgaltsgvhtfpavlqssglyslssvvtvpss nfgtqtytcnvdhkpsntkvdktverkccvec ppcpappvagpsvflfppkpkdtlmisrtpev tcvvvdvshedpevqfnwyvdgvevhnaktkp reeqfnstfrvvsvltvvhqdwlngkeykckv snkglpapiektisktkgqprepqvytlppsr eemtknqvsltclvkgfypsdiavewesngqp ennykttppmldsdgsfflyskltvdksrwqq gnvfscsvmhealhnhytqkslslspgk |
| Light Chain | DIQMTQSPSSLSASVGDRVTITC<u>RASQGISSW LA</u>WYQQKPEKAPKSLIY<u>AASSLQS</u>GVPSRFSG SGSGTDFTLTISSLQPEDFATYYC<u>QQYNSYPP TF</u>GGGTKVEIKrtvaapsvfifppsdeqlksg tasvvcllnnfypreakvqwkvdnalqsgnsq esvteqdskdstyslsstltlskadyekhkvy acevthqglsspvtksfnrgec |

TABLE 2B

Amino Acid Sequences for Antibody 18D8

| DESCRIPTION | SEQUENCE (Variable region in upper case, constant region in lower case, CDRs underlined) |
|---|---|
| Heavy Chian | EVQLVESGGGLVQPGRSLRLSCAASGFTFD<u>DY AMH</u>WVRQAPGKGLEWVS<u>GISWNSGSIGYADSV KG</u>RFTISRDNAKNSLYLQMNSLRAEDTALYYC AK<u>DQSTADYYFYYGMDV</u>WGQGTTVTVSSastk gpsvfplapcsrstsestaalgclvkdyfpep vtvswnsgaltsgvhtfpavlqssglyslssv vtvpssnfgtqtytcnvdhkpsntkvdktver kccvecppcpappvagpsvflfppkpkdtlmi srtpevtcvvvdvshedpevqfnwyvdgvevh naktkpreeqfnstfrvvsvltvvhqdwlngk eykckvsnkglpapiektisktkgqprepqvy tlppsreemtknqvsltclvkgfypsdiavew esngqpennykttppmldsdgsfflyskltvd ksrwqqgnvfscsvmhealhnhytqkslslsp gk |

TABLE 2B-continued

Amino Acid Sequences for Antibody 18D8

| DESCRIPTION | SEQUENCE (Variable region in upper case, constant region in lower case, CDRs underlined) |
|---|---|
| Light Chain | EIVVTQSPATLSLSPGERATLSC<u>RASQSVSSY LA</u>WYQQKPGQAPRLLIY<u>DASNRAT</u>GIPARFSG SGSGTDFTLTISSLEPEDFAVYYC<u>QQRSNWPT</u> FGQGTKVEIKrtvaapsvfifppsdeqlksgt asvvcllnnfypreakvqwkvdnalqsgnaqe svteqdskdstyslsstltlskadyekhkvya cevthqglsspvtksfnrgec |

TABLE 3

Summary of Certain in vitro Properties of Antibody 11D4

| Parameter | Activity µg/ml | (nM) |
|---|---|---|
| Affinity for OX40R: (Biacore) | | |
| $K_D$ | 0.07 | 0.48 |
| Off rate (kd) | | 5.7E−05 1/s |
| Binding to OX40R: | | |
| Fusion protein extracellular domain Saturation binding ($EC_{50}$): | 0.5 +/− 0.18 | 3.50 |
| CD3/CD28 stimulated T cells (N = 17) | 0.6 +/− 1.00 | 4.00 |
| OX40R + 300-19 cells (N = 5) | 0.2 +/− 0.16 | 1.70 |
| In vitro stimulation of OX40R + transfected cells (luciferase) ($EC_{50}$; N = 4) | 0.33 +/− 0.22 | 2.20 |
| Augmentation of T cell activity: | | |
| CD3 induced IL-2 production (N = 12) | 0.042 +/− 0.01 | 0.30 |
| Stimulation of IL-2 production by antigen-primed cells (N = 2) | 0.008 +/− 0.006 | 0.04 |
| Selectivity (binding) (CD40, CD137, CD271) | >100 µg/mL | >700.00 |

Values represent the mean +/− one SD

TABLE 4

Effect of Antibody 11D4 on Anti-CD3 Induced IL-2 Production by Primary Human T Cells

| $EC_{50}$ (µg/mL) | Max IL-2 (pg/mL) | ECmax (µg/mL) | Stimulation Index | Donor |
|---|---|---|---|---|
| 0.008 | 4831 | 0.05 | 3.8 | 1 |
| 0.011 | 5450 | 0.05 | 2.6 | 2 |
| 0.014 | 6571 | 0.5 | 2.3 | 3 |
| 0.014 | 7271 | 0.05 | 5.9 | 4 |
| 0.011 | 6313 | 0.05 | 9.1 | 5 |
| ND | ND | ND | 7.0 | 6 |
| 0.010 | 1006 | 0.05 | 4.8 | 7 |
| ND | ND | ND | 5.9 | 8 |
| ND | ND | ND | 25.4 | 9 |
| ND | ND | ND | 57.0 | 10 |
| ND | ND | ND | 8.3 | 11 |
| ND | ND | ND | 5.1 | 12 |
| ND | ND | ND | 2.7 | 13 |
| ND | ND | ND | 4.6 | 14 |
| 0.014 | 4687 | 0.05 | 6.0 | 15 |
| 0.014 | 3012 | 0.05 | 35.2 | 16 |
| ND | ND | ND | 21.4 | 17 |
| 0.029 | 2796 | 0.125 | 3.8 | 18 |
| 0.052 | 1718 | 0.125 | 5.5 | 19 |
| 0.020 | 14190 | 0.56 | 16.8 | 20 |
| 0.068 | 1611 | 1.67 | 7.9 | 21 |

Max IL-2: Amount of IL-2 produced with 11D4 at the ECmax over anti-CD3 alone
ECmax: Concentration of 11D4 producing the maximum level of IL-2 over anti-CD3 alone
Stimulation Index: Ratio of the maximum level of IL-2 produced with 11D4 vs the amount of IL-2 produced with anti-CD3 alone
ND = not determined.
Values for the last four donors (18-21) are from dose response curve done in 8-point 1:3 or 1:4 dilutions; all other values represent log dilution curves. The $EC_{50}$ from the 1:3 and 1:4 concentration curves was 0.042 +/− 0.01 ug/mL, N = 4.

TABLE 5

Effect of Antibody 11D4 on Anti-CD3 Induced IL-2 Production by Cynomolgus T Cells.

| $EC_{50}$ (µg/mL) | Max IL-2 Induced (pg/mL) | ECmax (µg/mL) | Stimulation index | Donor |
|---|---|---|---|---|
| 0.007 | 376 | 0.05 | 3.5x | 32750 |
| 0.002 | 116 | 0.05 | 2.2x | 2325 |
| ND | ND | ND | 2.0x | 32405 |
| 0.007 | 167 | 0.05 | 34.4 | 32081 |
| 0.011 | 978 | 0.005 | 5.6x | 32842 |
| ND | ND | ND | 6.3x | 2325 |
| 0.008 | 40 | 0.021 | 2.7x | 33081 |
| 0.031 | 168 | 0.062 | 5.0x | 33080 |
| 0.028 | 128 | 0.062 | 3.8x | 33062 |

Max IL-2: Amount of IL-2 produced with 11D4 at ECmax over anti-CD3 alone
ECmax: Concentration of 11D4 producing the maximum level of IL-2 over anti-CD3 alone
Stimulation Index: Ratio of the maximum IL-2 produced with 11D4 over the amount produced with anti-CD3 alone
ND = not determined Values for the last three donors (33081, 33080, and 33062) in Table 6 are from dose-response curve done in 8-point 1:3 dilutions. All other values represent log dilution curves. The $EC_{50}$ derived from those curves using 1:3 dilutions was 0.022+/−0.01; N=3.

TABLE 6

Human Tumor Growth Inhibition by Antibody 11D4 In SCID-beige Mice Engrafted with Human T cells and Dendritic Cells

| Tumor Type | Dosing with 11D4 | Study Duration | 10 mg/kg | 1.0 mg/kg | 0.1 mg/kg | 0.01 mg/kg |
|---|---|---|---|---|---|---|
| Raji: B cell lymphoma | Day 1 | 21 days | 64% | 42% | 27% | nd |
| Raji: B cell lymphoma | Day 1 | 21 days | nd | 75% | 42% | 8% |
| Lovo: colon carcinoma | Day 1 | 25 days | 76% | 44% | 20% | nd |
| Lovo: colon carcinoma | Day 1 | 25 days | 87% | 64% | 15% | nd |
| PC3: prostate | Day 1 | 27 days | 90% | 77% | 45% | nd |
| PC3: prostate | Day 1 | 27 days | 90% | 70% | 50% | nd |
| BT474: breast | Day 1 and 30 | 85 days | 98% | 85% | 46% | nd |

Values = % inhibition of tumor growth determined at study termination
nd = not detected

TABLE 7

Results of in vitro Studies with Antibody 18D8

| Parameter | Activity µg/ml | (nM) |
|---|---|---|
| Affinity for OX40R (Biacore): | | |
| $K_D$ | 0.49 | 3.38 |
| Off rate (kd) | | 2.9E−04 1/s |
| Binding to OX40R ($EC_{50}$): | | |
| Fusion protein extracellular domain | 0.034 +/− 0.01 | 0.23 |
| Saturation binding: | | |
| CD3/CD28 stimulated T cells (N = 4) | 1.06 +/− 0.51 | 7.30 |
| OX40R + 300-19 cells (N = 2) | 0.24 +/− 0.09 | 1.66 |
| Augmentation of T Cell Activity ($EC_{50}$): | | |
| CD3 induced IL-2 production (N = 4) | 0.049 +/− 0.06 | 0.33 |
| Stimulation of IL-2 production by antigen-primed cells (N = 1) | 0.014 +/− 0 | 0.10 |
| Selectivity (Binding to CD40, CD137, CD271): | >100 µg/mL | >700.00 |

Values for activity expressed in µg/ml represent the mean +/− one SD.

TABLE 8

Effect of Antibody 18D8 on Anti-CD3 Induced IL-2 Production by Primary Human T Cells.

| $EC_{50}$ (µg/mL) | Max IL-2 (pg/mL) | ECmax (µg/mL) | Stimulation Index | Donor |
|---|---|---|---|---|
| 0.013 | 1120 | 0.05 | 13.7 | LC |
| 0.024 | 4334 | 0.5 | 5.1 | TH |
| 0.024 | 2280 | 0.5 | 5.4 | KO |
| 0.135 | 1356 | 0.5 | 2.4 | RN |

Max IL-2: Amount of IL-2 produced with 18D8 at the ECmax over anti-CD3 alone.
ECmax: Concentration of 18D8 producing the maximum level of IL-2 over anti-CD3 alone.
Stimulation Index: Ratio of the maximum IL-2 produced with 18D8 over the amount produced with anti-CD3 alone.
Values represent log dilution curves.

TABLE 9

Inhibition of Human Tumor Growth by Antibody 18D8 in SCID-beige Mice

| Tumor Type | Dosing with 18D8 | Study Duration | Dose Level of 18D8 (mg/kg) 10 | 1.0 | 0.1 | 0.01 |
|---|---|---|---|---|---|---|
| Raji: B cell lymphoma | Day 1 | 23 days | 73% | 73% | 11% | nd |
| Raji: B cell lymphoma | Day 1 | 24 days | 54% | 59% | nd | nd |
| PC3: prostate | Day 1 | 24 days | 88% | 90% | 42% | nd |

Values = % inhibition of tumor growth determined at study termination
nd = not determined

We claim:

1. An isolated nucleic acid molecule comprising a nucleic acid sequence that encodes a heavy chain or an antigen-binding fragment thereof, and a light chain or an antigen-binding fragment thereof of an antibody that specifically binds OX40R, wherein said antibody comprises:
   (a) a heavy chain variable region ($V_H$) comprising:
      a $V_H$ CDR1 region comprising an amino acid sequence of SEQ ID NO: 13,
      a $V_H$ CDR2 region comprising an amino acid sequence of SEQ ID NO: 14, and
      a $V_H$ CDR3 region comprising an amino acid sequence of SEQ ID NO: 15; and a light chain variable region ($V_L$) comprising:
      a $V_L$ CDR1 region comprising an amino acid sequence of SEQ ID NO: 16,
      a $V_L$ CDR2 region comprising an amino acid sequence of SEQ ID NO: 17, and
      a $V_L$ CDR3 region comprising an amino acid sequence of SEQ ID NO: 18;
   (b) a heavy chain variable region comprising an amino acid sequence of SEQ ID NO: 19; and a light chain variable region comprising an amino acid sequence of SEQ ID NO: 20; or
   (c) a heavy chain comprising an amino acid sequence of SEQ ID NO: 21; and a light chain comprising an amino acid sequence of SEQ ID NO: 22.

2. A vector comprising the isolated nucleic acid molecule according to claim 1.

3. The vector according to claim 2, further comprising an expression control sequence operably linked to said isolated nucleic acid molecule.

4. The vector according to claim 2, wherein said vector is selected from the group consisting of a plasmid expression vector, a retrovirus expression vector, an adenovirus expression vector, and an adeno-associated virus expression vector.

5. A host cell comprising said vector according to claim 2.

6. The host cell according to claim 5, wherein said host cell is selected from the group consisting of a mammalian cell, an insect cell, a plant cell, a bacterial cell, and a yeast cell.

7. A method for producing a monoclonal antibody or an antigen-binding fragment thereof that specifically binds human OX40R, comprising culturing said host cell according to claim 5 under suitable conditions and recovering said monoclonal antibody or said antigen-binding fragment.

8. An isolated nucleic acid molecule comprising:
   (a) a nucleic acid sequence of SEQ ID NO: 23;
   (b) a nucleic acid sequence of SEQ ID NO: 24; or
   (c) a nucleic acid sequence of (a) and a nucleic acid sequence of (b).

9. A vector comprising the isolated nucleic acid molecule according to claim 8.

10. The vector according to claim 9, further comprising an expression control sequence operably linked to said isolated nucleic acid molecule.

11. The vector according to claim 9, wherein said vector is selected from the group consisting of a plasmid expression vector, a retrovirus expression vector, an adenovirus expression vector, and an adeno-associated virus expression vector.

12. A host cell comprising said vector according to claim 9.

13. The host cell according to claim 12, wherein said host cell is selected from the group consisting of a mammalian cell, an insect cell, a plant cell, a bacterial cell, and a yeast cell.

14. A method for producing a monoclonal antibody or an antigen-binding fragment thereof that specifically binds human OX40R, comprising culturing said host cell according to claim 12 under suitable conditions and recovering said monoclonal antibody or said antigen-binding fragment.

15. An isolated nucleic acid molecule comprising a nucleic acid sequence encoding the amino acid sequences of SEQ ID NOs: 13, 14, and 15.

16. The isolated nucleic acid molecule according to claim 15, wherein said nucleic acid sequence further encodes the amino acid sequences of SEQ ID NOs: 16, 17, and 18.

* * * * *

SEQUENCE LISTING

<160> NUMBER OF SEQ ID NOS: 24

<210> SEQ ID NO 1
<211> LENGTH: 5
<212> TYPE: PRT
<213> ORGANISM: Human

<400> SEQUENCE: 1

Ser Tyr Ser Met Asn
1               5

<210> SEQ ID NO 2
<211> LENGTH: 17
<212> TYPE: PRT
<213> ORGANISM: Human

<400> SEQUENCE: 2

Tyr Ile Ser Ser Ser Ser Ser Thr Ile Asp Tyr Ala Asp Ser Val Lys
1               5                   10                  15

Gly

<210> SEQ ID NO 3
<211> LENGTH: 9
<212> TYPE: PRT
<213> ORGANISM: Human

<400> SEQUENCE: 3

Glu Ser Gly Trp Tyr Leu Phe Asp Tyr
1               5

<210> SEQ ID NO 4
<211> LENGTH: 11

<212> TYPE: PRT
<213> ORGANISM: Human

<400> SEQUENCE: 4

Arg Ala Ser Gln Gly Ile Ser Ser Trp Leu Ala
1               5                   10

<210> SEQ ID NO 5
<211> LENGTH: 7
<212> TYPE: PRT
<213> ORGANISM: Human

<400> SEQUENCE: 5

Ala Ala Ser Ser Leu Gln Ser
1               5

<210> SEQ ID NO 6
<211> LENGTH: 9
<212> TYPE: PRT
<213> ORGANISM: Human

<400> SEQUENCE: 6

Gln Gln Tyr Asn Ser Tyr Pro Pro Thr
1               5

<210> SEQ ID NO 7
<211> LENGTH: 118
<212> TYPE: PRT
<213> ORGANISM: Human

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Ser Gly Trp Tyr Leu Phe Asp Tyr Trp Gly Gln Gly Thr
            100                 105                 110

Leu Val Thr Val Ser Ser
        115

<210> SEQ ID NO 8
<211> LENGTH: 107
<212> TYPE: PRT
<213> ORGANISM: Human

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

```
Tyr Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Pro
                 85                  90                  95

Thr Phe Gly Gly Gly Thr Lys Val Glu Ile Lys
                100                 105

<210> SEQ ID NO 9
<211> LENGTH: 444
<212> TYPE: PRT
<213> ORGANISM: Human

<400> SEQUENCE: 9

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
             35                  40                  45

Ser Tyr Ile Ser Ser Ser Ser Thr Ile Asp Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Glu Ser Gly Trp Tyr Leu Phe Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
210                 215                 220

Pro Pro Cys Pro Ala Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320
```

```
Ser Asn Lys Gly Leu Pro Ala Pro Ile Glu Lys Thr Ile Ser Lys Thr
            325                 330                 335

Lys Gly Gln Pro Arg Glu Pro Gln Val Tyr Thr Leu Pro Pro Ser Arg
        340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 10
<211> LENGTH: 214
<212> TYPE: PRT
<213> ORGANISM: Human

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 354
<212> TYPE: DNA
```

<210> SEQ ID NO 11
<211> LENGTH: 354
<212> TYPE: DNA
<213> ORGANISM: Human

<400> SEQUENCE: 11

```
gaggtgcagc tggtggagtc tgggggaggc ttggtacagc cggggggtc cctgagactc      60
tcctgtgcag cctctggatt caccttcagt agctatagca tgaactgggt ccgccaggct    120
ccagggaagg gctggagtg ggtttcatac attagtagta gtagtagtac catagactac    180
gcagactctg tgaagggccg attcaccatc tccagagaca atgccaagaa ctcactgtat    240
ctgcaaatga acagcctgag agacgaggac acggctgtgt attattgtgc gagagaaagc    300
ggctggtacc tctttgacta ctggggccag ggaaccctgg tcaccgtctc ctca          354
```

<210> SEQ ID NO 12
<211> LENGTH: 321
<212> TYPE: DNA
<213> ORGANISM: Human

<400> SEQUENCE: 12

```
gacatccaga tgacccagtc tccatcctca ctgtctgcat ctgtaggaga cagagtcacc     60
atcacttgtc gggcgagtca gggtattagc agctggttag cctggtatca gcagaaacca   120
gagaaagccc ctaagtccct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacag tataatagtt accctcccac tttcggcgga   300
gggaccaagg tggagatcaa a                                              321
```

<210> SEQ ID NO 13
<211> LENGTH: 5
<212> TYPE: PRT
<213> ORGANISM: Human

<400> SEQUENCE: 13

Asp Tyr Ala Met His
1               5

<210> SEQ ID NO 14
<211> LENGTH: 17
<212> TYPE: PRT
<213> ORGANISM: Human

<400> SEQUENCE: 14

Gly Ile Ser Trp Asn Ser Gly Ser Ile Gly Tyr Ala Asp Ser Val Lys
1               5                   10                  15
Gly

<210> SEQ ID NO 15
<211> LENGTH: 15
<212> TYPE: PRT
<213> ORGANISM: Human

<400> SEQUENCE: 15

Asp Gln Ser Thr Ala Asp Tyr Tyr Phe Tyr Tyr Gly Met Asp Val
1               5                   10                  15

<210> SEQ ID NO 16
<211> LENGTH: 11
<212> TYPE: PRT
<213> ORGANISM: Human

<400> SEQUENCE: 16

```
Arg Ala Ser Gln Ser Val Ser Ser Tyr Leu Ala
1               5                   10
```

<210> SEQ ID NO 17
<211> LENGTH: 7
<212> TYPE: PRT
<213> ORGANISM: Human

<400> SEQUENCE: 17

```
Asp Ala Ser Asn Arg Ala Thr
1               5
```

<210> SEQ ID NO 18
<211> LENGTH: 8
<212> TYPE: PRT
<213> ORGANISM: Human

<400> SEQUENCE: 18

```
Gln Gln Arg Ser Asn Trp Pro Thr
1               5
```

<210> SEQ ID NO 19
<211> LENGTH: 124
<212> TYPE: PRT
<213> ORGANISM: Human

<400> SEQUENCE: 19

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Phe Tyr Tyr Gly Met Asp
            100                 105                 110

Val Trp Gly Gln Gly Thr Thr Val Thr Val Ser Ser
        115                 120
```

<210> SEQ ID NO 20
<211> LENGTH: 106
<212> TYPE: PRT
<213> ORGANISM: Human

<400> SEQUENCE: 20

```
Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80
```

```
Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 21
<211> LENGTH: 450
<212> TYPE: PRT
<213> ORGANISM: Human

<400> SEQUENCE: 21

Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
                35                  40                  45

Ser Gly Ile Ser Trp Asn Ser Gly Ser Ile Gly Tyr Ala Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Phe Tyr Tyr Gly Met Asp
                100                 105                 110

Val Trp Gly Gln Gly Thr Thr Val Thr Val Ser Ser Ala Ser Thr Lys
                115                 120                 125

Gly Pro Ser Val Phe Pro Leu Ala Pro Cys Ser Arg Ser Thr Ser Glu
            130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Asn Phe Gly Thr Gln Thr Tyr Thr Cys Asn
                195                 200                 205

Val Asp His Lys Pro Ser Asn Thr Lys Val Asp Lys Thr Val Glu Arg
            210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Phe Arg
            290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
```

```
                  340                 345                 350
Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 22
<211> LENGTH: 213
<212> TYPE: PRT
<213> ORGANISM: Human

<400> SEQUENCE: 22

Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 23
<211> LENGTH: 372
<212> TYPE: DNA
<213> ORGANISM: Human
```

```
<400> SEQUENCE: 23
gaagtgcagc tggtggagtc tgggggaggc ttggtacagc ctggcaggtc cctgagactc        60
tcctgtgcag cctctggatt cacctttgat gattatgcca tgcactgggt ccggcaagct       120
ccagggaagg gcctggaatg ggtctcaggt attagttgga atagtggtag cataggctat       180
gcggactctg tgaagggccg attcaccatc tccagagaca acgccaagaa ctccctgtat       240
ctgcaaatga acagtctgag agctgaggac acggccttgt attactgtgc aaaagatcag       300
agtacagctg attactactt ctactacggt atggacgtct ggggccaagg gaccacggtc       360
accgtctcct ca                                                          372

<210> SEQ ID NO 24
<211> LENGTH: 318
<212> TYPE: DNA
<213> ORGANISM: Human

<400> SEQUENCE: 24
gaaattgtgg tgacacagtc tccagccacc ctgtctttgt ctccagggga aagagccacc        60
ctctcctgca gggccagtca gagtgttagc agctacttag cctggtacca acagaaacct       120
ggccaggctc ccaggctcct catctatgat gcatccaaca gggccactgg catcccagcc       180
aggttcagtg gcagtgggtc tgggacagac ttcactctca ccatcagcag cctagagcct       240
gaagattttg cagtttatta ctgtcagcag cgtagcaact ggccgacgtt cggccaaggg       300
accaaggtgg aaatcaaa                                                    318
```